US012345669B2

(12) United States Patent
Swager et al.

(10) Patent No.: US 12,345,669 B2
(45) Date of Patent: *Jul. 1, 2025

(54) ETHYLENE SENSOR

(71) Applicant: MASSACHUSETTS INSTITUTE OF TECHNOLOGY, Cambridge, MA (US)

(72) Inventors: Timothy M. Swager, Newton, MA (US); Birgit Esser, Cambridge, MA (US); Jan M. Schnorr, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/681,313

(22) Filed: Aug. 18, 2017

(65) Prior Publication Data

US 2018/0067065 A1    Mar. 8, 2018

Related U.S. Application Data

(63) Continuation of application No. 13/832,430, filed on Mar. 15, 2013, now Pat. No. 9,739,737.

(60) Provisional application No. 61/614,834, filed on Mar. 23, 2012.

(51) Int. Cl.
*G01N 27/12* (2006.01)
*G01N 33/00* (2006.01)

(52) U.S. Cl.
CPC .......... *G01N 27/12* (2013.01); *G01N 27/125* (2013.01); *G01N 33/0047* (2013.01); *G01N 27/127* (2013.01); *Y10T 29/49117* (2015.01); *Y10T 436/216* (2015.01)

(58) Field of Classification Search
CPC ....................................................... G01N 27/12
USPC ........................... 422/90; 436/142, 149, 151
See application file for complete search history.

(56) References Cited

U.S. PATENT DOCUMENTS

| | | | | |
|---|---|---|---|---|
| 2,648,598 A | * | 8/1953 | Stitt | G01N 31/22 422/87 |
| 4,410,632 A | | 10/1983 | Dilley | |
| 4,414,839 A | | 11/1983 | Dilley | |
| 6,105,416 A | | 8/2000 | Nelson | |
| 6,240,767 B1 | | 6/2001 | Nelson | |
| 7,291,503 B2 | * | 11/2007 | Swager | B82Y 30/00 436/149 |

(Continued)

FOREIGN PATENT DOCUMENTS

| | | |
|---|---|---|
| JP | 2010-25719 A | 2/2010 |
| JP | 2010-38840 A | 2/2010 |

(Continued)

OTHER PUBLICATIONS

Wosnick, J. H. et al, Current Opinion in Chemical Biology 2000, 4, 715-720.*

(Continued)

*Primary Examiner* — Arlen Soderquist
(74) *Attorney, Agent, or Firm* — Wolf, Greenfield & Sacks, P.C.

(57) ABSTRACT

A sensor device can include a transition metal complex capable of interacting with a carbon-carbon multiple bond moiety. The sensor can detect the fruit-ripening hormone ethylene with high sensitivity.

20 Claims, 17 Drawing Sheets

(56) References Cited

U.S. PATENT DOCUMENTS

| | | | | |
|---|---|---|---|---|
| 7,318,908 | B1* | 1/2008 | Dai | G01N 33/551 |
| | | | | 422/50 |
| 7,801,687 | B1* | 9/2010 | Li | G01N 27/127 |
| | | | | 977/921 |
| 8,147,901 | B2* | 4/2012 | Jung | B82Y 15/00 |
| | | | | 427/58 |
| 8,951,473 | B2* | 2/2015 | Wang | B82Y 40/00 |
| | | | | 422/68.1 |
| 9,267,908 | B2* | 2/2016 | Wang | G01N 27/127 |
| 9,739,737 | B2* | 8/2017 | Swager | G01N 27/12 |
| 2002/0040805 | A1* | 4/2002 | Swager | B82Y 15/00 |
| | | | | 174/110 A |
| 2003/0109056 | A1 | 6/2003 | Vossmeyer et al. | |
| 2003/0178607 | A1* | 9/2003 | Swager | B82Y 10/00 |
| | | | | 252/582 |
| 2003/0198849 | A1 | 10/2003 | Hampden-Smith et al. | |
| 2004/0213701 | A1 | 10/2004 | Hattori | |
| 2004/0235184 | A1* | 11/2004 | Swager | B82Y 30/00 |
| | | | | 436/149 |
| 2005/0000830 | A1* | 1/2005 | Glatkowski | B82Y 30/00 |
| | | | | 204/400 |
| 2005/0031985 | A1 | 2/2005 | Burstyn et al. | |
| 2005/0072213 | A1* | 4/2005 | Besnard | G01N 27/127 |
| | | | | 73/31.06 |
| 2007/0048180 | A1* | 3/2007 | Gabriel | B82Y 15/00 |
| | | | | 422/400 |
| 2007/0145356 | A1* | 6/2007 | Amlani | B82Y 10/00 |
| | | | | 257/40 |
| 2007/0292896 | A1* | 12/2007 | Strano | B82Y 15/00 |
| | | | | 435/7.9 |
| 2007/0295203 | A1 | 12/2007 | Shekarriz | |
| 2008/0030352 | A1* | 2/2008 | Shaw | G01N 27/127 |
| | | | | 340/579 |
| 2008/0093226 | A1 | 4/2008 | Briman | |
| 2008/0095922 | A1* | 4/2008 | Jung | B82Y 15/00 |
| | | | | 427/58 |
| 2008/0113301 | A1* | 5/2008 | Jung | B82Y 15/00 |
| | | | | 430/315 |
| 2008/0206890 | A1* | 8/2008 | Burstyn | C07F 1/005 |
| | | | | 436/525 |
| 2008/0221806 | A1* | 9/2008 | Bryant | G01N 27/127 |
| | | | | 702/22 |
| 2008/0308407 | A1 | 12/2008 | Rostovtsev et al. | |
| 2009/0017571 | A1* | 1/2009 | Nuckolls | C12Q 1/002 |
| | | | | 422/68.1 |
| 2009/0084162 | A1* | 4/2009 | Besnard | G01N 27/127 |
| | | | | 73/31.06 |
| 2010/0086439 | A1* | 4/2010 | Yamanaka | G01N 21/77 |
| | | | | 422/52 |
| 2010/0089772 | A1 | 4/2010 | Deshusses | |
| 2010/0116682 | A1* | 5/2010 | Neuzil | G01N 27/403 |
| | | | | 205/419 |
| 2010/0133465 | A1* | 6/2010 | Kwon | B01F 17/0007 |
| | | | | 252/74 |
| 2010/0179054 | A1 | 7/2010 | Swager | |
| 2010/0262034 | A1* | 10/2010 | Kawata | A61B 5/097 |
| | | | | 600/532 |
| 2011/0089051 | A1 | 4/2011 | Wang | |
| 2011/0102002 | A1 | 5/2011 | Riehl | |
| 2011/0217544 | A1 | 9/2011 | Young et al. | |
| 2012/0012472 | A1 | 1/2012 | Ahrens et al. | |
| 2015/0247832 | A1 | 9/2015 | Swager | |
| 2016/0011135 | A1* | 1/2016 | Wang | B82Y 15/00 |
| | | | | 205/781 |
| 2016/0077048 | A1 | 3/2016 | Azad | |
| 2016/0169810 | A1 | 6/2016 | Swager | |
| 2019/0086360 | A1 | 3/2019 | Swager et al. | |
| 2021/0255159 | A1 | 8/2021 | Swager et al. | |

FOREIGN PATENT DOCUMENTS

| | | |
|---|---|---|
| JP | 2010107310 | 5/2010 |
| JP | 2010-523452 A | 7/2010 |
| JP | 2011-80798 A | 4/2011 |
| JP | 2010/106898 A1 | 9/2012 |
| KR | 10-0723429 B1 | 5/2007 |
| WO | 2005/120205 | 12/2005 |
| WO | 2010/106898 A1 | 9/2010 |

OTHER PUBLICATIONS

Dias, H. V. R. et al, Organometallics 2002, 21, 1466-1473.*
Cho, S. M. et al, IEEE Sensors 2004, 701-704.*
Li, R. W. C. et al, Sensors and Actuators B 2008, 131, 646-651.*
Rahman, M. A. et al, Sensors 2008, 8, 118-141.*
Li, R. W. C. et al, Materials Science and Engineering C 2009, 29, 426-429.*
Benvenho, A. R. V. et al, Sensors and Actuators B 2009, 136, 173-176.*
Kang, Y. K. et al, Nano Letters 2009, 9, 1414-1418.*
Kamonsawas, J. et al, Sensors 2010, 10, 5590-5603.*
Salehi-Khojin, A. et al, ACS Nano 2011, 5, 153-158.*
Yang, J.-S. et al, Journal of the American Chemical Society 1998, 120, 11864-11873.*
Levitsky, I. A. et al, Macromolecules 2001, 34, 2315-2319.*
Basiuk, E. V. et al, Nano Letters 2002, 2, 1249-1252.*
Li, J. et al, Nano Letters 2003, 3, 929-933.*
Crespo, G. A. et al, Analytical Chemistry 2009, 81, 676-681.*
Moraes, F. C. et al, Electroanalysis 2010, 22, 1586-1591.*
Roth, S. et al, Faraday Discussions of the Chemical Society 1989, 88, 223-233.*
Ley, K. D. et al, Coordination Chemistry Reviews 1998, 171, 287-307.*
Jones, W. E. et al, "Metal-Organic Conducting Polymers: Photoactive Switching in Molecular Wires" in Multimetallic and Macromolecular Inorganic Photochemistry Ramamurthy, V. et al, Eds, 1999, 1-30.*
Chen, L. et al, Proceedings of the National Academy of Sciences of the United States of America 1999, 96, 12287-12292.*
Huber, C. et al, Journal of the American Chemical Society 2001, 123, 3857-3863.*
Pron, A. et al, Progress In Polymer Science 2002, 27, 135-190.*
Kushmerick, J. G. et al, Annals of the New York Academy of Sciences 2003, 1006, 277-290.*
Dai, L., "Conducting Polymers" in Intelligent Macromolecules for Smart Devices. Engineering Materials and Processes, Springer, London, 2004, 41-80.*
Holt, A. L. et al, Journal of CHemical Physics 2005, 123, paper 044704, 7 pages.*
Yang, J.-S. et al, Journal of the American Chemical Society 2006, 128, 14109-14119 and 14 pages of supporting information.*
Morikita, T. et al, Reactive & Functional Polymers 2008, 68, 1483-1491.*
Esser, B. et al, Angewandte Chemie International Edition 2010, 49, 8872-8875 and 14 pages of supporting information.*
Mcqueen, E. W. et al, Journal of the American Chemical Society 2009, 131, 17554-17556.*
Nobusawa, K. et al, Supramolecular Chemistry 2011, 23, 102-105.*
Lee, H.-J. et al, Carbon, 2011, 49, 5150-5157.*
Fagan, P. J. et al, Science 1991, 252, 1160-1162.*
Durgun, E. et al, Journal of Physical Chemistry B 2004, 108, 575-582.*
Lee, Y. et al, Small 2005, 1, 975-979 and 4 supplemental Information pages.*
Wang, D. et al, Journal of the American Chemical Society 2006, 128, 15078-15079.*
Hatton, R. A. et al, Langmuir 2007, 23, 6424-6430.*
Hu, C. et al, Langmuir 2008, 24, 8890-8897.*
Peng, X. et al, Advanced Materials 2009, 21, 625-642.*
Kong, L. et al, Analyst, 2010, 135, 368-374.*
Zhang, Y.-H. et al, Nanotechnology 2010, 21, paper 065201, 7 pages.*

(56) References Cited

OTHER PUBLICATIONS

Zhang, Y. et al, Physical Review B 2010, 81, paper 085201, 5 pages.*
Wang, Y. et al, Journal of Materials Chemistry 2011, 21, 3779-3787.*
Sarkar, S. et al, Chemical Science 2011, 2, 1326-1333.*
Albrecht, M. et al, Angewandte Chemie International Edition 2001, 40, 3750-3781.*
Lu, Y. et al, Chemical Physics Letters 2004, 391, 344-348.*
Banerjee, S. et al, Advanced Materials 2005, 17, 17-29.*
Lu, Y. et al, Journal of Electroanalytical Chemistry 2006, 593, 105-110.*
Cattanach, K. et al, Nanotechnology 2006, 17, 4123-4128.*
Peng, G. et al, Nano Letters 2008, 8, 3631-3635.*
Peng, G. et al, Nano Letters 2009, 9, 1362-1368.*
Yeung, C. S. et al, Journal of Nanotechnology 2010, article 801789, 42 pages.*
Wang, F. et al, Journal of the American Chemical Society 2011, 133, 11181-11193.*
Munakata, M. et al, Inorganic Chemistry 1986, 25, 2622-2627.*
Curran, S. A. et al, Advanced Materials 1998, 10, 1091-1093.*
Chen, J. et al, Journal of the American Chemical Society 2002, 124, 9034-9035.*
Star, A. et al, Macromolecules 2003, 36, 553-560.*
Liu, L. et al, Chemical Physics Letters 2003, 367, 747-752.*
Yim, W.-L. et al, Journal of Physical Chemistry B 2003, 107, 9363-9369.*
Green, O. et al, Journal of the American Chemical Society 2004, 126, 5952-5953.*
Star, A. et al, Advanced Materials 2004, 16, 2049-2052.*
Price, B. K. et al, Journal of the American Chemical Society 2005, 127, 14867-14870.*
Li, J. et al, IEEE Sensors Journal 2006, 6, 1047-1051.*
Padigi, S. K. et al, Biosensors and Bioelectronics 2007, 22, 829-837.*
Shekarriz, R., Proceedings of the Florida State Horticultural Society 2007, 120, 251-255.*
Manoukian, M. et al, NASA Tech Briefs Jul. 2007, 6-7.*
Karkkanen, A. et al, IEEE Sensors 2007 Conference 2007, 547-549.*
Lee, J.-H. et al, Sensors and Actuators B 2008, 129, 628-631.*
Wang, F. et al, Angewandte Chemie—International Edition 2008, 47, 8394-8396 and 11 pages of supporting informaton.*
Wang, Y. et al, Journal of Sensors 2009, Article ID 493904, 24 pages.*
Kou, X. et al, Dalton Transactions 2009, 7529-7536.*
Cintroon, M. S. et al, Inorganic Chemistry 2012, 51, 2737-2746.*
Freire, R. S. et al, Analyst 2002, 127, 1502-1506.*
Ng, Z. et al, ACS Nano 2009, 3, 2103-2114.*
Osorio, E. A. et al, Nano Letters 2010, 10, 105-110.*
Zanella, R. et al, Journal of Physical Chemistry B 2005, 109, 16290-16295. (Year: 2005).*
Bernhardt, P. V. et al, Australian Journal of Chemistry 2003, 56, 239-258. (Year: 2003).*
Espinosa, E. H. et al, Thin Solid Films 2007, 515, 8322-8327. (Year: 2007).*
Kauffman, D. R. et al, Angewandte Chemie International Edition 2008, 47, 6550-6570. (Year: 2008).*
Leghrib, R. et al, Procedia Chemistry 2009, 1, 168-171. (Year: 2009).*
Tofighy, M. A. et al, Journal of Hazardous Materials 2011, 185, 140-147. (Year: 2011).*
Liu, Y.-T. et al, Carbon 2011, 49, 3371-3375 with 19 pasges of supplementary material. (Year: 2011).*
Ryu, Y. et al, Carbon 2011, 49, 4745-4751. (Year: 2011).*
Li, E. Y. et al, ACS Nano 2011, 5, 9726-9736. (Year: 2011).*
Banerjee, S. et al, Chemistry a European Journal 2003, 9, 1898-1908. (Year: 2003).*
Lee, C. Y. et al, Journal of the American Chemical Society 2008, 130, 1766-1773 with 6 pages of supporting information. (Year: 2008).*
Capek, I., Advances in Colloid and Interface Science 2009, 150, 63-89. (Year: 2009).*
Cid, C. C. et al, Sensors and Actuators B 2009, 141, 97-103. (Year: 2009).*
Penza, M. et al, Sensors and Actuators B 2010, 144, 387-394. (Year: 2010).*
Penza, m> et al, Nanotechnology 2011, 22, paper 125502, 8 pages. (Year: 2011).*
Shirsat, M. D. et al, Journal of Physical Chemistry C 2012, 116, 3845-3850. (Year: 2012).*
Paterno, L. G. et al, Journal of Applied Polymer Science 2002, 83, 1309-1316.
Virji, S. et al, Nano Letters 2004, 4, 491-496.
An, K. H. et al, Advanced Materials 2004, 16, 1005-1009.
Wanna, Y. et al, Journal of Nanoscience and Nanotechnology 2006, 6, 3893-3896.
Rowe, M. P. et al, Analytical Chemistry 2007, 79, 1164-1172.
Wang, F. et al, Journal of the American Chemical Society 2008, 130, 5392-5393.
Flores, J. A. et al, Inorganic Chemistry 2008, 47, 4448-4450.
Rajesh et al, Sensors and Actuators B 2009, 136, 275-286.
Pattananuwat, P. et al, Advanced Materials Research 2010, 93-94, 459-462.
Lu, J. et al, Nanotechnology 2010, 21, paper 255501, 10 pages.
Pattananuwat, P. et al, Materials Science Forum 2011, 695, 336-339.
Thompson, J. S. et al, Journal of the American Chemical Society 1983, 105, 3522-3527.
McQuade, D. T. et al, Chemical Reviews 2000, 100, 2537-2574.
Dai, L. et al, Pure and Applied Chemistry 2002, 74, 1753-1772.
Pettinari, C. et al, Polyhedron 2004, 23, 451-469.
McNeil, A, J. et al, Journal of the American Chemical Society 2006, 128, 12426-12427.
Pistor, P. et al, Sensors and Actuators B 2007, 123, 153-157.
Korostynska, O. et al, Sensors 2007, 7, 3027-3042.
Dias, H. V. R. et al, European Journal of Inorganic Chemistry 2008, 509-522.
Esser, B. et al, Angewandte Chemie International Edition 2010, 49, 8872-8875.
Esser, B. et al, Angewandte Chemie International Edition 2012, 51,5752-5756.
International Search Report and Written Opinion of the International Searching Authority dated Dec. 6, 2013 for PCT/US2013/031851.
International Preliminary Report on Patentability for PCT/US2013/31851 mailed Sep. 23, 2014.
Office Action from CA 2,868149, Dec. 14, 2018.
Office Action from CN 201380023698.2, Feb. 2, 2019.
Office Action from MX MX/a/2014/011421, Jan. 4, 2018.
Jun, L. et al., "Carbon Nanotube Nanoelectrode Array for Ultrasensitive DNA Detection," Nano Letters vol. 3(5), 2003, 597-602.
Winkler, K. et al., "Electrochemically formed two-component films comprised of fullerene and transition-metal components," Comptes Rendu-Chimie, vol. 9 (7-8), 2006, 928-943.
Zhang, T. et al., "Recent progress in carbon nanotube-based gas sensors," Nanotechnology, vol. 19 (33), 2008.
Office action mailed in Brazilian Application No. 112014023454-0 on Nov. 8, 2019.
Office Action mailed in Israeli Patent Application No. 234778 on May 14, 2018.
Office Action mailed in Mexican Patent Application No. MX/a/2014/011421 on Aug. 13, 2019.
Office Action mailed in Canadian Patent Application No. 2,868,149 on Jan. 30, 2020.
Office Action mailed in Korean Patent Application No. 10-2014-7029641 on Feb. 6, 2020.

* cited by examiner

FIG. 9A
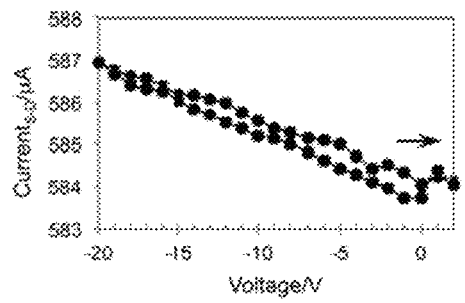
FIG. 9B
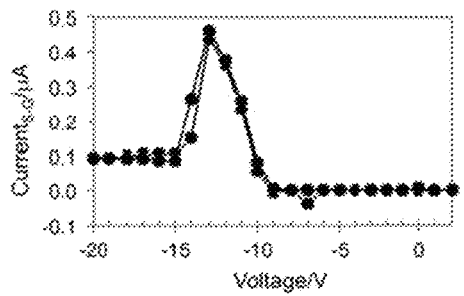
FIG. 9C
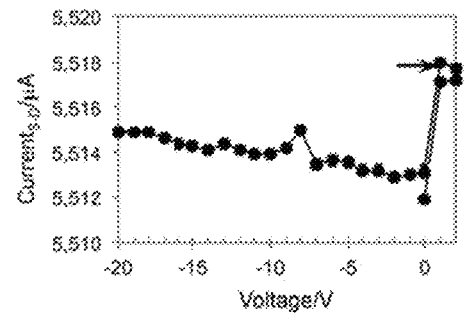
FIG. 9D
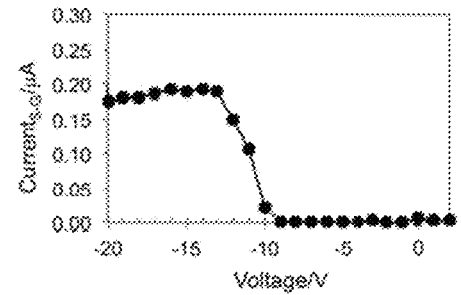
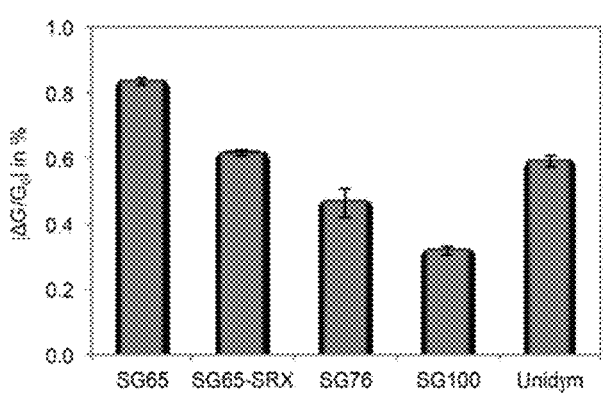
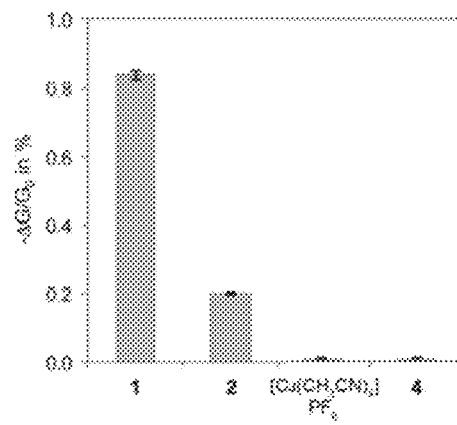
FIG. 10

Exposure to ethylene diluted with nitrogen gas, 40 s each.

ETHYLENE SENSOR

CLAIM OF PRIORITY

This application is a continuation of U.S. application Ser. No. 13/832,430, filed Mar. 15, 2013, which claims priority to U.S. Provisional Application No. 61/614,834, filed Mar. 23, 2012, each of which is incorporated by reference in its entirety.

FEDERALLY SPONSORED RESEARCH OR DEVELOPMENT

This invention was made with government support under W911NF-07-D-0004 awarded by the U.S. Army Research Office. The government has certain rights in this invention.

TECHNICAL FIELD

This invention relates to ethylene sensors, materials for use in ethylene sensors, and methods of making and using these.

BACKGROUND

Ethylene, the smallest plant hormone, plays a role in many developmental processes in plants. It initiates the ripening of fruit, promotes seed germination and flowering, and is responsible for the senescence of leaves and flowers. As fruits and vegetables start ripening, ethylene is produced and emitted, and the internal ethylene concentration in some fruits is used as a maturity index to determine the time of harvest. In some vegetables and fruits, such as bananas, exposure to ethylene gas results in a continuation of the ripening process after harvesting, thus the monitoring of ethylene gas in storage rooms is important to avoid the deterioration of ethylene sensitive produce.

SUMMARY

A reversible chemoresistive sensor able to detect sub-ppm concentrations of analytes such as ethylene is described. The ethylene-responsive material has high selectivity towards ethylene and is prepared simply in few steps from commercially available materials. The sensing mechanism can take advantage of the high sensitivity in resistance of single-walled carbon nanotubes (SWCNTs or SWNTs) to changes in their electronic surroundings, and the binding of a copper (I) complex to carbon-carbon multiple bonds.

In one aspect, a sensor includes a conductive material comprising a carbon-carbon multiple bond moiety, the conductive material being in electrical communication with at least two electrodes; and a transition metal complex capable of interacting with a carbon-carbon multiple bond moiety.

The conductive material can include a carbon nanotube. The transition metal complex can be capable of forming a stable complex with ethylene. The transition metal complex can be associated with the carbon nanotube by coordination of the transition metal to the carbon-carbon multiple bond moiety. The transition metal complex can be associated with the carbon nanotube by a covalent link between the carbon nanotube and a ligand of the transition metal complex. The transition metal complex can be associated with the carbon nanotube by a polymer which is non-covalently associated with the carbon nanotube. The transition metal complex can be bound to the carbon-carbon multiple bond moiety of the conductive material.

The transition metal complex can have formula (I):

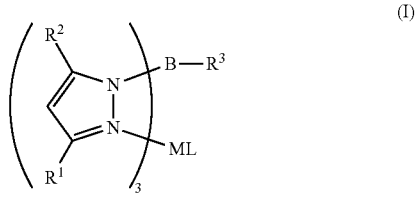

where:
M can be a transition metal; each $R^1$, independently, can be H, halo, alkyl, or haloalkyl; each $R^2$, independently, can be H, halo, alkyl, haloalkyl, or aryl; $R^3$ can be H or alkyl; and L can be absent or represent a ligand.

The transition metal complex can have formula (II):

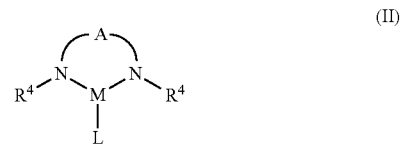

where:
M can be a transition metal; each $R^4$, independently, can be alkyl, haloalkyl, aryl, or trialkylsilyl; A can be —CH($R^5$)—X—CH($R^5$)— wherein X is N or CH, and each $R^5$, independently, can be H, halo, alkyl, or haloalkyl; or A can be —P($R^6$)$_2$—, wherein each $R^6$, independently, is alkyl; and L can be absent or represent a ligand.

The transition metal complex can have the formula:

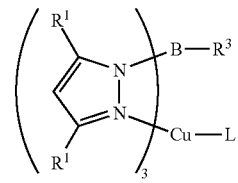

where:
each $R^1$, independently, can be H, methyl, or trifluoromethyl; each $R^2$, independently, can be H, methyl, trifluoromethyl, or phenyl; $R^3$ can be H or methyl; and L can be absent, a thiol, or a carbon-carbon multiple bond.

In another aspect, a method of sensing an analyte includes exposing a sensor to a sample, the sensor including: a conductive material comprising a carbon-carbon multiple bond moiety, the conductive material being in electrical communication with at least two electrodes; and a transition metal complex capable of interacting with a carbon-carbon multiple bond moiety; and measuring an electrical property at the electrodes.

The sample can be a gas. The electrical property can be resistance or conductance. The analyte can be ethylene. The conductive material can include a carbon nanotube. The transition metal complex can be capable of forming a stable complex with ethylene. The transition metal complex can be associated with the carbon nanotube by coordination of the transition metal to the carbon-carbon multiple bond moiety.

The transition metal complex can be associated with the carbon nanotube by a covalent link between the carbon nanotube and a ligand of the transition metal complex. The transition metal complex can be associated with the carbon nanotube by a polymer which is non-covalently associated with the carbon nanotube. The transition metal complex can be bound to the carbon-carbon multiple bond moiety of the conductive material.

In the method, the transition metal complex can have formula (I) or formula (II) as described above. In the method, the transition metal complex can have the formula:

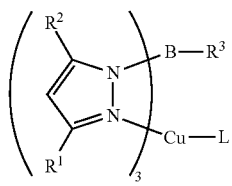

where:
each $R^1$, independently, can be H, methyl, or trifluoromethyl; each $R^2$, independently, can be H, methyl, trifluoromethyl, or phenyl; $R^3$ can be H or methyl; and L can be absent, a thiol, or a carbon-carbon multiple bond.

A composite including the transition metal complex and the carbon-carbon multiple bond moiety, for example, SWCNT, can be mixed with a polymer, for example, in the form of polystyrene beads.

In another aspect, a method of making a sensor includes forming a complex including a conductive material comprising a carbon-carbon multiple bond moiety, and a transition metal complex capable of interacting with a carbon-carbon multiple bond moiety; and placing the conductive material in electrical communication with at least two electrodes.

In another aspect, a method of making of making a sensor includes forming a complex including a conductive material comprising a carbon-carbon multiple bond moiety, a transition metal complex capable of interacting with a carbon-carbon multiple bon moiety, and one or more polymers; and placing the conductive material in electrical communication with at least two electrodes.

The method can include spray drying the complex at a temperature to obtain a viscous conductive material, and the viscous material can be placed in electrical communication with at least two electrodes. The temperature can be between 10° and 210° C., 140° C. and 210° C., 180° C. to 210° C., for example, above 200° C. The spray drying can take place in an inert atmosphere, such as nitrogen.

The transition metal can be copper. The electrodes can be gold. The sensor can be configured to sense ethylene. The complex can be a Cu(I) scorpionate. The complex can be Cu(I) scorpionate 1.

The placing of the conductive material can include applying the conductive material and one or more polymers onto at least two electrodes by drop-casting, spin-coating, screen-printing, inkjet printing, spreading, painting, or pelletizing and abrading the material onto a surface, or combinations thereof. The conductive material and polymer (or polymers) can be applied simultaneously or in sequence.

In some embodiments, the polymer can be a hydrophobic polymer such as polyethylene or polystyrene. In some embodiments, the polymer can be a fluorinated polymer, which can be partially fluorinated or perfluorinated (e.g. polyvinylidene fluoride, Nafion). In some embodiments, the polymer can contain ionic groups (e.g. Nafion). In some embodiments, the polymer can be conjugated or partially conjugated polymers including polyacetylene, polyphenylenevinylene, polythiophene, polypyrrole or polyaniline, optionally including electron donating groups, such as alkoxy groups (e.g. Poly[2-methoxy-5-(2-ethylhexyloxy)-1, 4-phenylenevinylene]). In some embodiments, the polymer can be a mixture of polymers, including conjugated or nonconjugated mixtures or copolymers.

In some embodiments, the polymer can be selected from the group consisting of a polyethylene, a polystyrene, a poly(ethylene oxide), a polyvinylidene fluoride, a Nafion, a polyphenylenevinylene, and combinations thereof.

In some embodiments, the method can include combining the complex mixture with a selector, such as a transition metal salt, for example, Ag(OTf) or $Pd(OCOCF_3)_2$.

Other aspects, embodiments, and features will be apparent from the following description, the drawings, and the claims.

BRIEF DESCRIPTION OF THE DRAWINGS

FIGS. 9A-9D are graphs showing results of FET measurements: FIG. 9A, source-drain current for pristine SWCNTs; FIG. 9B, gate leakage current for pristine SWCNTs; FIG. 9C, source-drain current for 1-SWCNT; and FIG. 9D, gate leakage current for 1-SWCNT. The voltage was swept from 0 to +2 V to −20V.

FIG. 10 shows responses to 20 ppm ethylene of (left) 1-SWCNT devices made from different types of SWCNTs and (right) devices made from 1-SWCNT, 2-SWCNT, SWCNTs with $[Cu(CH_3CN)_4]PF_6$ and 4-SWCNT.

FIG. 11A, survey scans of 1, 2, and 1-SWCNT; and FIG. 11B, high resolution scans of the Cu 2p region of 1, 2, and 1-SWCNT.

DETAILED DESCRIPTION

Figure 1:
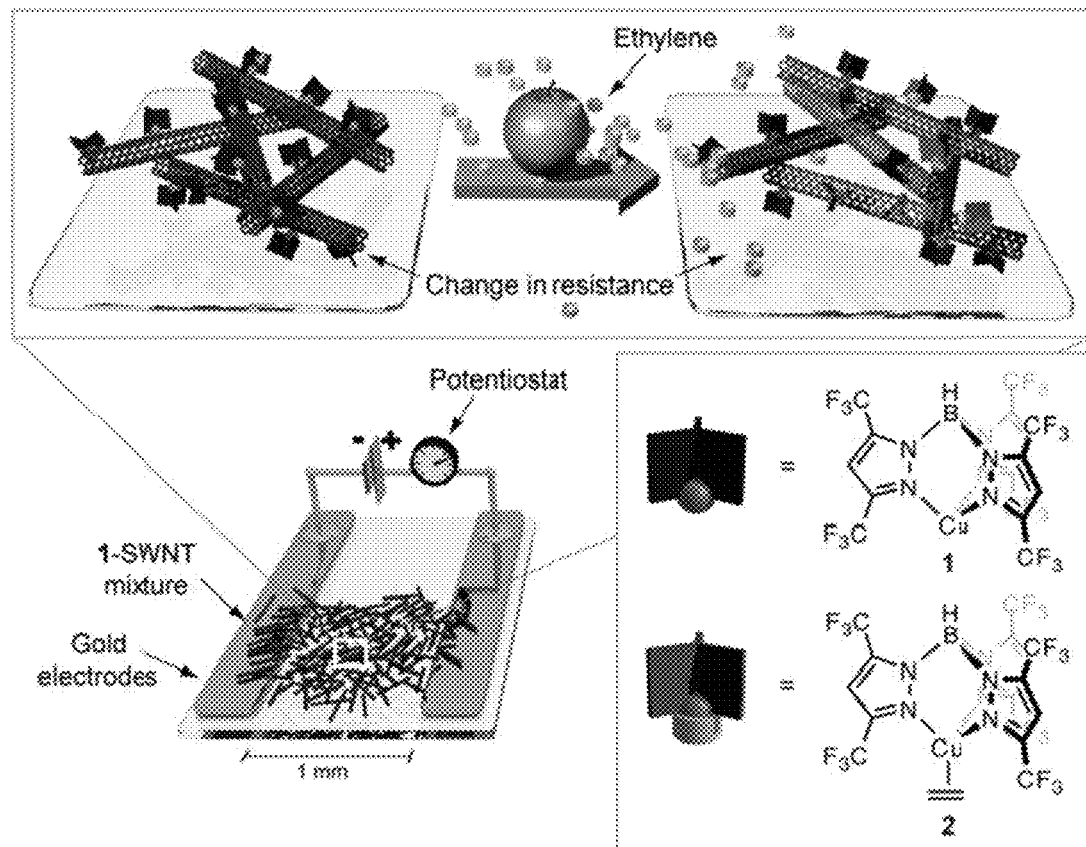
FIG. 1 is a schematic illustration of ethylene detection by a chemoresistive sensor. A mixture of single-walled carbon nanotubes (SWCNTs or SWNTs) and copper complex 1 is drop-cast between gold electrodes, and the change in resistance in response to ethylene exposure is measured. The copper complexes partly bind to ethylene molecules, forming ethylene complex 2, and resulting in a resistance change.

Because of its small size and lack of polar chemical functionality, ethylene is generally hard to detect. Traditionally, gas chromatography and photoacoustic spectroscopy have been used to measure ethylene concentrations. See, for example, H. Pham-Tuan, et al., J. Chromatogr. A 2000, 868, 249-259; and M. Scotoni, et al., Appl. Phys. B 2006, 82, 495-500; each of which is incorporated by reference in its entirety. Both techniques suffer from the disadvantage of being operationally impractical and do not allow for real-time measurements. Other sensing systems that have been suggested use electrochemical or chemoresistive methods, magnetoelastic sensing, photoluminescence quenching, and fluorescence turn-on. All of these systems have drawbacks such as high cost, impracticability, or insufficient sensitivity towards ethylene. See, e.g., L. R. Jordan, et al., Analyst 1997, 122, 811-814; Y. Pimtong-Ngam, et al., Sens. Actuators A 2007, 139, 7-11; M. A. G. Zevenbergen, et al., Anal. Chem. 2011, 83, 6300-6307; R. Zhang, et al., Sensors 2002, 2, 331-338; O. Green, et al., J. Am. Chem. Soc. 2004, 126, 5952-5953; and B. Esser, et al., Angew. Chem. Int. Ed. 2010, 49, 8872-8875; each of which is incorporated by reference in its entirety. In addition, gas-sampling tubes based on a colorimetric reaction are available (see A. A. Kader, M. S. Reid, J. F. Thompson, in Postharvest Technology of Horticultural Crops, (Ed: A. A. Kader), University of California, Agricultural and Natural Resources, Publication 3311, 2002, pp. 39 ff., 55 ff., 113 ff., 149 ff., 163 ff, which is incorporated by reference in its entirety).

In general, a sensor (e.g., a chemoresistive or FET sensor) includes a conductive material including a carbon-carbon multiple bond moiety, the conductive material being in electrical communication with at least two electrodes; and a transition metal complex capable of interacting with a carbon-carbon multiple bond moiety. A measurable property of the sensor (e.g. resistance, conductivity, or other electrical property measured between electrodes) changes upon exposure of the sensor to an analyte. The transition metal complex can be mixed with a particulate material, such as polymer beads (e.g., polystyrene beads) or other material to increase the surface area of an active sensing region of the sensor or to exploit the potential of the particulate material to act as a preconcentrator for the analyte. The sensor can be an element of an array sensor that can include one or more of the sensor including a conductive material including a carbon-carbon multiple bond moiety. For example, the array can include 2, 3, 4, 5, 6, 7, 8, 9, 10, 11, 12, 13, 14, 15, 16, 17, 18, 19, 20, 25, 50, or more sensor elements.

The analyte can have an electron-rich moiety capable of interacting with the transition metal complex. For example, the electron-rich moiety can include a carbon-carbon multiple bond; a carbon-nitrogen multiple bond; or a lone pair of electrons (e.g., as may be found in the C=O moiety of an aldehyde or ketone). In some cases, the analyte includes a carbon-carbon double bond, such as is found in ethylene, propylene, and other alkenes; or the analyte can include a carbon-carbon triple bond, such as is found in acetylene, propyne, or other alkynes.

The conductive material can include a conductive carbon-containing material, including but not limited to carbon nanotubes, conductive polymers, or combinations thereof, and further including additional components such as other polymers, binders, fillers, or the like. The conductive carbon-containing material can include, for example, SWCNTs, MWNTs, conductive polymers such as a poly(acetylene), a poly(phenylene vinylene), a poly(pyrrole), a poly(thiophene), a poly(aniline), a poly(phenylene sulfide), or other conductive polymers, or combinations thereof. A conductive polymer can include a copolymer or mixtures of polymers. The conductive polymer can include a carbon-carbon multiple bond moiety.

Polymers or polymer materials, as used herein, refer to extended molecular structures comprising a backbone (e.g., non-conjugated backbone, conjugated backbone) which optionally contain pendant side groups, where "backbone"

refers to the longest continuous bond pathway of the polymer. In some embodiments, the polymer is substantially non-conjugated or has a non-conjugated backbone. In some embodiments, at least a portion of the polymer is conjugated, i.e. the polymer has at least one portion along which electron density or electronic charge can be conducted, where the electronic charge is referred to as being "delocalized." A polymer may be "pi-conjugated," where atoms of the backbone include p-orbitals participating in conjugation and have sufficient overlap with adjacent conjugated p-orbitals. It should be understood that other types of conjugated polymers may be used, such as sigma-conjugated polymers.

The polymer can be a homo-polymer or a co-polymer such as a random co-polymer or a block co-polymer. In one embodiment, the polymer is a block co-polymer. The polymer compositions can vary continuously to give a tapered block structure and the polymers can be synthesized by either step growth or chain growth methods.

The number average molecular weight of the polymer may be selected to suit a particular application. As used herein, the term "number average molecular weight (Mn)" is given its ordinary meaning in the art and refers to the total weight of the polymer molecules in a sample, divided by the total number of polymer molecules in a sample. Those of ordinary skill in the art will be able to select methods for determining the number average molecular weight of a polymer, for example, gel permeation chromatography (GPC). In some cases, the GPC may be calibrated vs. polystyrene standards. In some cases, the number average molecular weight of the polymer is at least about 10,000, at least about 20,000, at least about 25,000, at least about 35,000, at least about 50,000, at least about 70,000, at least about 75,000, at least about 100,000, at least about 110,000, at least about 125,000, or greater.

In an analyte-free state, the transition metal complex can interact with the carbon-carbon multiple bond moiety of the conductive carbon-containing material, for example, by a coordination of the transition metal atom(s) with carbon atoms belonging to the conductive carbon-containing material. The sensor can have a baseline level of a measurable property in the analyte-free state.

When exposed to the analyte, at least a portion of the transition metal complex can bind to the analyte, e.g., to the electron-rich moiety such as a carbon-carbon double bond, changing the nature and/or extent of interaction between the transition metal complex and the conductive material. This change is reflected in a change in the measurable property of the sensor; in other words, the sensor produces a measurable response when exposed to the analyte.

The sensor can provide high sensitivity to the analyte. For example, a gaseous analyte such as ethylene can be detected at levels of less than 100 ppm, less than 50 ppm, less than 20 ppm, less than 10 ppm, less than 1 ppm, less than 5 ppm, less than 2 ppm, less than 1 ppm, less than 0.5 ppm, or less. The sensor can also provide a linear response to analyte concentration, such that an unknown concentration of the analyte can be determined based on the strength of the sensor response.

The transition metal complex can include a transition metal capable of interacting with a carbon-carbon multiple bond moiety. Such transition metals include but are not limited to Fe, Ru, Os, Co, Rh, Ir, Ni, Pd, Pt, Cu, Ag, or Au. The transition metal complex can include a transition metal capable of interacting with a carbon-carbon multiple bond moiety, coordinated by a multidentate ligand with coordinating atoms selected from N and P, and optionally coordinated by an additional ligand L, which can be, for example, a carbon-carbon multiple bond moiety.

In some cases, the transition metal complex can have formula (I) or (II):

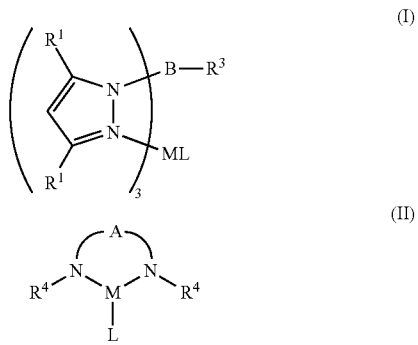

In formula (I), M can be a transition metal; each $R^1$, independently, can be H, halo, alkyl, or haloalkyl; each $R^2$, independently, can be H, halo, alkyl, haloalkyl, or aryl; $R^3$ can be H or alkyl; and L can be absent or represent a ligand. The ligand can in some cases be a η-2 carbon-carbon multiple bond moiety or a carbon-heteroatom multiple bond moiety.

In formula (II), M can be a transition metal; each $R^4$, independently, can be alkyl, haloalkyl, aryl, or trialkylsilyl. A can be —CH($R^5$)—X—CH($R^5$)— where X can be N or CH, and each $R^5$, independently, can be H, halo, alkyl, or haloalkyl, or A can be —P($R^6$)$_2$—, where each $R^6$, independently, can be alkyl; and L can be absent or represent a ligand.

Alkyl is a straight or branched hydrocarbon chain containing 1 to 16 (preferably, 1 to 10; more preferably 1 to 6) carbon atoms, which can be substituted or unsubstituted. The substituent can be a bond linking one group with an adjacent moiety or the conductive material. The alkyl group can be optionally interrupted by —O—, —N($R^a$)—, —N($R^a$)—C(O)—O—, —O—C(O)—N($R^a$)—, —N($R^a$)—C(O)—N($R^b$)—, or —O—C(O)—O—. Each of $R^a$ and $R^b$, independently, can be hydrogen, alkyl, alkenyl, alkynyl, alkoxy, hydroxylalkyl, hydroxyl, or haloalkyl. In certain embodiments, the alkyl group can be optionally substituted with $C_{1-4}$ alkyl, $C_{2-4}$ alkenyl, $C_{2-4}$ alkynyl, $C_{1-4}$ alkoxy, hydroxyl, halo, amino, thio, alkylthio, arylthio, aralkylthio, acylthio, nitro, cyano, $C_{3-5}$ cycloalkyl, 3-5 membered heterocycloalkyl, monocyclic aryl, 5-6 membered heteroaryl, $C_{1-4}$ alkylcarbonyloxy, $C_{1-4}$ alkyloxycarbonyl, $C_{1-4}$ alkylcarbonyl, or formyl.

In some embodiments, any of $R^1$, $R^2$, $R^3$, $R^4$, $R^5$ or $R^6$, independently, can be covalently linked to another moiety, including the conductive material, for example, a carbon nanotube or a polymer.

The transition metal is a transition metal with one or more valence level d-electrons. In formulas (I) and (II), M can be Fe, Ru, Os, Co, Rh, Ir, Ni, Pd, Pt, Cu, Ag, or Au; in some cases, M can be Cu, Ag, or Au.

In some cases, the transition metal complex can have the formula:

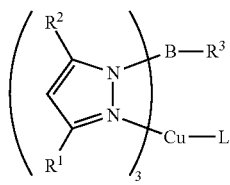

where L can be absent or represents a ligand, each $R^1$, independently, can be H, methyl, or trifluoromethyl; each $R^2$, independently, can be H, methyl, trifluoromethyl, or phenyl; and $R^3$ can be H or alkyl. L can be absent, a thiol, an amine, a carbon-heteroatom multiple bond (for example, MeCN) or a carbon-carbon multiple bond, e.g., an alkene, an alkyne, or a carbon-carbon multiple bond moiety of a conductive carbon-containing material. In some cases, each $R^1$ and each $R^2$ are trifluoromethyl, $R^3$ is H, and L is absent or ethylene or MeCN. The transition metal complex can be complex 1, copper(I) hydrotris[3,5-bis(trifluoromethyl)pyrazol-1-yl]borate:

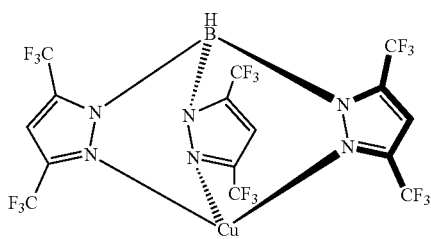

1

In some cases, the transition metal complex can have the formula:

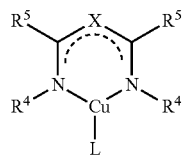

where L can be absent or represents a ligand, X can be N or CH, each $R^4$, independently, can be alkyl (e.g., methyl, isopropyl, t-butyl), haloalkyl, or aryl (e.g., phenyl, pentafluorophenyl, or 2,5-dimethylphenyl), and each $R^5$, independently can be H, halo, alkyl (e.g., methyl, ethyl, propyl, isopropyl), or haloalkyl (e.g., trifluoromethyl, perfluoropropyl). L can be absent, a thiol, an amine, or a carbon-carbon multiple bond, e.g., an alkene, an alkyne, or a carbon-carbon multiple bond moiety of a conductive carbon-containing material.

In some cases, X can be N, each $R^5$ can be perfluoropropyl, and each $R^4$ can be perfluorophenyl. In some cases, X can be CH, each $R^5$ can be methyl, and each $R^4$ can be 2,5-dimethylphenyl.

In some cases, the transition metal complex can have the formula:

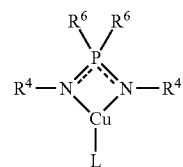

where L can be absent or represents a ligand; each $R^4$, independently, can be trialkylsilyl (e.g., trimethylsilyl); and each $R^6$, independently, can be alkyl (e.g., isopropyl, t-butyl) or haloalkyl. L can be absent, a thiol, an amine, or a carbon-carbon multiple bond, e.g., an alkene, an alkyne, or a carbon-carbon multiple bond moiety of a conductive carbon-containing material.

In some cases, each $R^6$ is t-butyl and each $R^4$ is trimethylsilyl.

In some embodiments, the conductive material includes SWCNTs. The transition metal complex can interact with carbon-carbon double bond moieties in the nanotube framework. When exposed to the analyte, the analyte can bind to the transition metal complex, displacing it from the carbon-carbon double bond moieties in the nanotube framework, causing a change in electrical properties (e.g., resistance) of the SWCNTs.

Optionally, the SWCNTs can be polymer-wrapped SWCNTs. For example, SWCNTs can be wrapped with a poly(thiophene). The poly(thiophene) can include pendant groups or side chains, which can bear a transition metal binding group such as, for example, a thiol. The transition metal binding group can interact with the transition metal complex. In this way, the transition metal complex interacts with the conductive material via pendant groups on a polymer-wrapped SWCNT.

Optionally, the transition metal complex is covalently linked to the conductive material. Many conductive carbon-containing materials can be functionalized; for example, carbon nanotubes can be functionalized with a variety of groups. For example, SWCNTs can be functionalized so as to bear a transition metal binding group such as, for example, a thiol. The transition metal binding group can interact with the transition metal complex. In this way, the transition metal complex interacts with the conductive material via covalent functional groups. In certain embodiments, the transition metal complex can be associated with the carbon nanotube, for example, through a covalent or non-covalent interaction. For example, a linker can be attached to the boron or other part of the ligand of the transition metal complex, which can be covalently bound to the carbon nanotube.

A carbon nanotube based system for ethylene sensing is illustrated schematically in FIG. 1. The ethylene sensitive material is an intimate mixture of SWCNTs with a copper(I) complex 1 based upon a fluorinated tris(pyrazolyl) borate ligand, which is able to interact with the surface of carbon nanotubes, thereby influencing their conductivity. Upon exposure to ethylene, 1 binds to ethylene and forms complex 2, which has a decreased interaction with the SWCNT surface. The result of this transformation is an increase in resistance of the SWCNT network. Complex 2 is one of the most stable copper-ethylene complexes known. See, e.g., H. V. R. Dias, et al., Organometallics 2002, 21, 1466-1473; and H. V. R. Dias, J. Wu, Eur. J. Inorg. Chem. 2008, 509-522; each of which is incorporated by reference in its entirety. It is not easily oxidized under ambient conditions and is stable in high vacuum. Compound 1 has been employed in the detection of ethylene in fluorescence schemes. See B. Esser, et al., Angew. Chem. Int. Ed. 2010, 49, 8872-8875, which is incorporated by reference in its entirety.

EXAMPLES

Fabrication

Figure 2A:
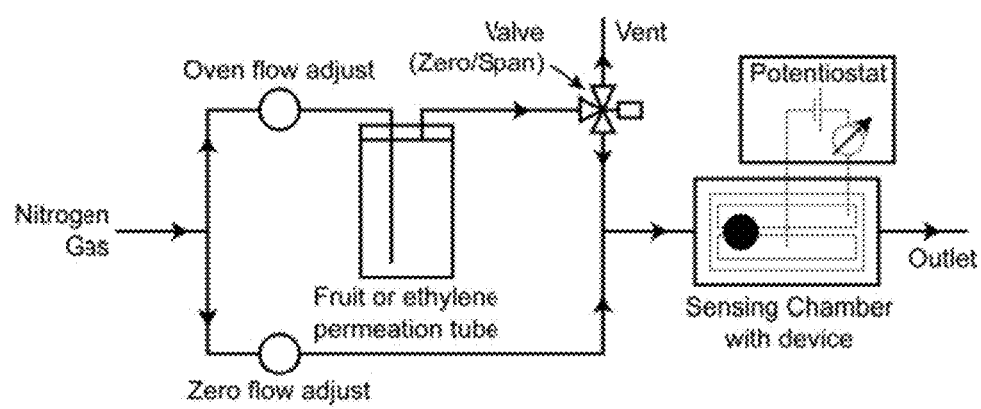
FIG. 2A is a schematic illustration of an experimental setup for sensing measurements. A continuous gas flow is directed through the device chamber. The gas stream can be switched between nitrogen gas ("Zero" mode) or the nitrogen gas analyte mixture ("Span" mode), in which the gas stream runs through the flow chamber containing the analyte (ethylene) or a piece of fruit.
Figure 2B:
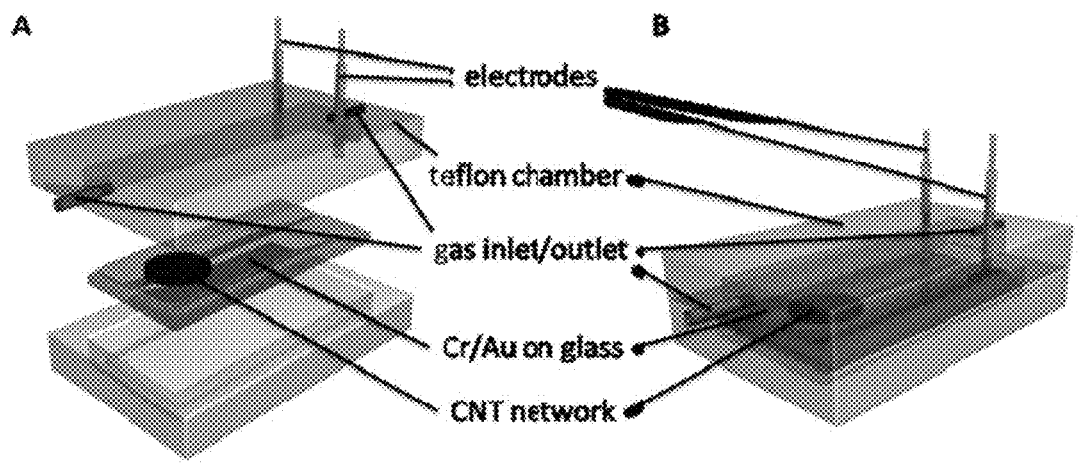
FIG. 2B is a schematic illustration of a gas flow chamber.
Figure 3A:
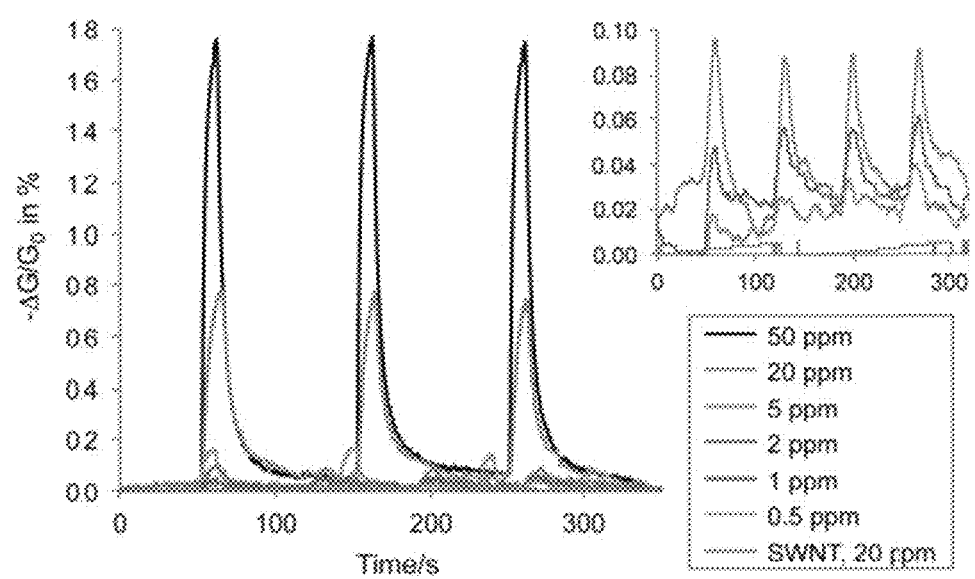
FIG. 3A shows relative responses of 1-SWCNT devices to 0.5, 1, 2, 5, 20, and 50 ppm ethylene diluted with nitrogen gas and of pristine SWCNT to 20 ppm ethylene (the inset shows the responses of 1-SWCNT to 0.5, 1, and 2 ppm and of SWCNT to 20 ppm.
Figure 3B:
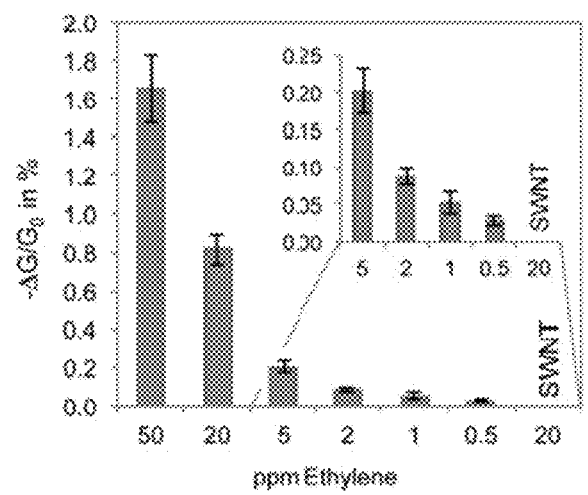
FIG. 3B shows average responses from three different devices each.
Figure 3C:
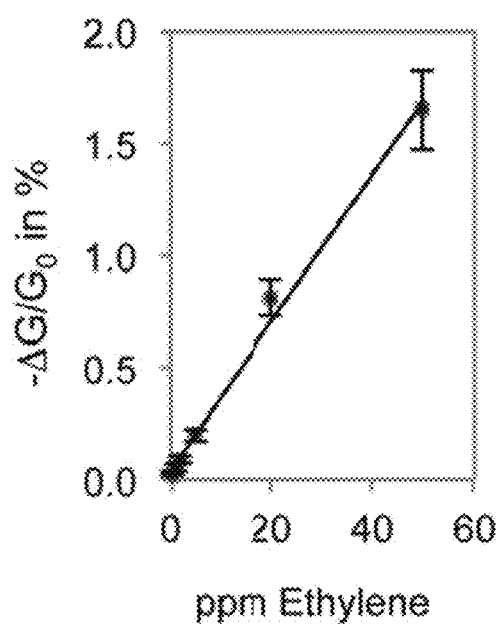
FIG. 3C shows a plot of average response vs. ethylene concentration.

In a typical experiment 1 was ultrasonicated with SWCNTs in a mixture of o-dichlorobenzene and toluene (2:3). Devices were prepared by drop-casting the resulting dispersion onto glass slides with pre-deposited gold electrodes (as shown in FIG. 1). The experimental setup for sensing measurements is shown in FIG. 2A. The device was enclosed in a gas flow chamber (FIG. 2B), with its electrodes connected to a potentiostat. The analyte-gas mixture was produced in a gas generator, in which a stream of nitrogen gas was split into two parts, one of which as led through a flow chamber containing an ethylene permeation tube or a piece of fruit. During a measurement, a continuous gas stream of constant flow rate, which could be switched between dinitrogen and the analyte-dinitrogen mixture, was directed over the device. The results from exposing 1-SWCNT devices to low concentrations of ethylene are shown in FIGS. 3A-3C. Ethylene concentrations of less than 1 ppm were detected, and measurements up to 50 ppm were performed. For many commodities, 1 ppm is the concentration at which ripening occurs at the maximum rate. Within the range of concentrations measured (0.5-50 ppm), a linear change in response was observed (see FIG. 3C).

Devices made from pristine SWCNTs showed no response to the same concentrations of ethylene (see FIGS. 3A-3C). Further controls, in which [Cu(CH$_3$CN)$_4$]PF$_6$ or the sodium equivalent of 1 (Cu replaced by Na) were employed instead of 1 did not respond to ethylene either (see below). Employing the ethylene complex 2 resulted in device sensitivity towards 20 ppm ethylene, however, the response amounted to only ~25% of that of 1-SWCNT devices (see below). In optimizing the ratio of 1 to SWCNT we found that a large excess of 1 (ratio of 1 to SWCNT carbon atoms=1:6) resulted in the best sensitivity. Different types of commercially available SWCNTs were tested in the devices (see below). The best results were obtained with SWCNTs of small diameter, namely SWCNTs containing >50% of (6,5) chirality. The stronger curvature of the carbon nanotube surface is believed to enhance the interaction between 1 and the SWCNT.

Figure 4:
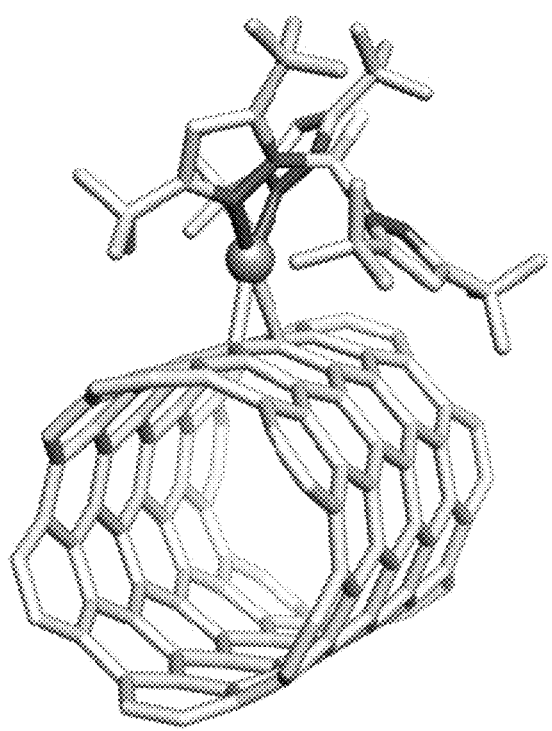
FIG. 4 shows the optimized structure of 3, in which 1 is coordinatively bound to a (6,5) SWCNT fragment (B3LYP/6-31G*, LanL2DZ for Cu; hydrogen atoms at the ends of the SWCNT fragment and on the pyrazol rings have been omitted for clarity).

Upon exposure to ethylene, a reversible increase in resistance was observed. This was ascribed to a mechanism as shown in FIG. 1, where the interaction of 1 with the SWCNT surface induces doping of the nanotubes. When complexes 1 bind to ethylene, this doping effect is diminished, and hence an increase in resistance is measured. In order to rationalize the interaction between 1 and the SWCNT surface, model calculations using density functional theory were performed. The structure of complex 3, where the copper center in 1 is bound to the surface of a short segment of a (6,5) SWCNT was optimized using the B3LYP functional with the 6-31G* basis set for main group elements and LanL2DZ for Cu. The optimized structure of 3 is shown in FIG. 4. Steric interactions forced one of the pyrazol rings of the ligand to be twisted in such a way that a trigonal planar coordination results for the Cu center. In an isodesmic equation, the binding strength of 1 to a (6,5) SWCNT fragment (3) was compared to the binding in 2. It was found that 2 is strongly favored over 3. Since reversible responses to ethylene were observed, the copper complexes 1 are believed to not completely dissociate from the SWCNTs, but bind the ethylene molecules in an associative fashion.

Figure 5:
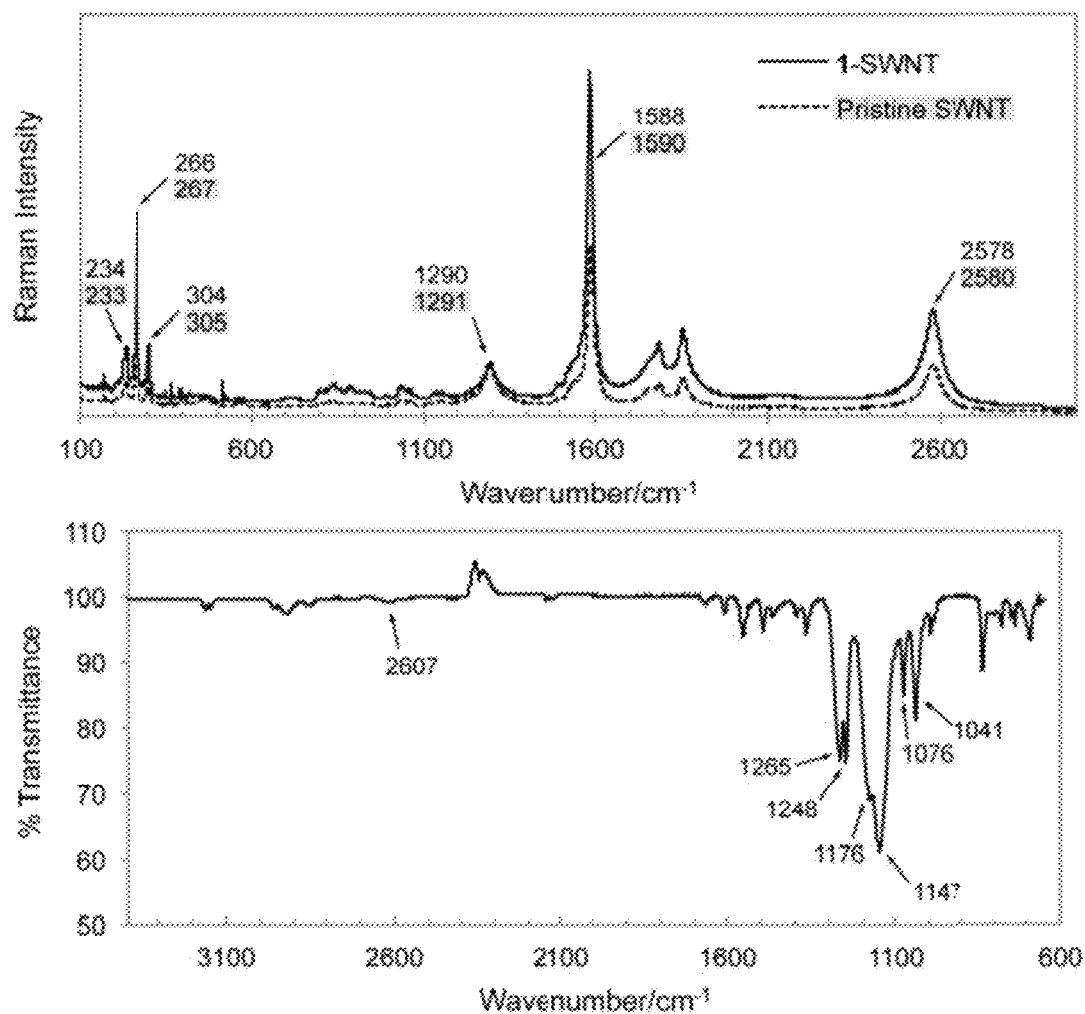
FIG. 5, top: Raman spectra of 1-SWCNT and pristine SWCNT (dashed line; laser energy 785 nm); bottom: IR spectrum of 1-SWNT.

The Raman and IR spectra of 1-SWCNT are shown in FIG. 5. Upon introduction of 1 into the SWCNT network a slight shift of the G and G' bands in the Raman spectrum to lower energies is observed, which can be indicative of p-type doping. See, e.g., A. Jorio, M. Dresselhaus, R. Saito, G. F. Dresselhaus, in *Raman Spectroscopy in Graphene Related Systems*, Wiley-VCH, Weinheim, Germany 2011, pp. 327 ff, which is incorporated by reference in its entirety. The IR spectrum of 1-SWCNT was dominated by the C—F stretching modes of the ligand between 1080-1260 cm$^{-1}$. The $v_{BH}$ shift was found at 2607 cm$^{-1}$. X-ray photoelectron spectroscopy (XPS) measurements were used to confirm the ratio of 1 to SWCNTs and to investigate the oxidation state of the copper centers, which can undergo oxidation to copper(II). A ratio of 1:22 was found for $C_{SWCNT}$:Cu (based on the Cu 2p peak, see below for data). In high resolution scans the characteristic pattern for copper(I) was observed, consisting of two peaks due to spin-orbit coupling at 932 and 952 eV.

In order to investigate the sensing mechanism, field-effect transistor (FET) devices were prepared with 1-SWCNT or pristine SWCNT. A device architecture with interdigitated Au electrodes (10 μm gap) on Si with 300 nm SiO$_2$ was used. The source-drain potential was kept at a constant bias of 0.1 V, while the source-gate potential was scanned between +2 and −20 V. A slight linear increase in conductance was observed towards negative gate voltages (see below for data), however, no strong gate effect. This lack of a measurable shift in the turn-on voltage may be the result of the fact that the charge injection (doping) differences were very small and/or due to device geometry and the nature of the nanotube network. In those cases where strong turn-on SWCNT FET responses are observed at negative gate voltages usually more highly ordered nanotube networks were employed. See, e.g., B. L. Allen, et al., Adv. Mater. 2007, 19, 1439-1451; R. Martel, et al., Appl. Phys. Lett. 1998, 73, 2447-2449; and S. Auvray, et al., Nano Lett. 2005, 5, 451-455, each of which is incorporated by reference in its entirety.

Figure 6A:
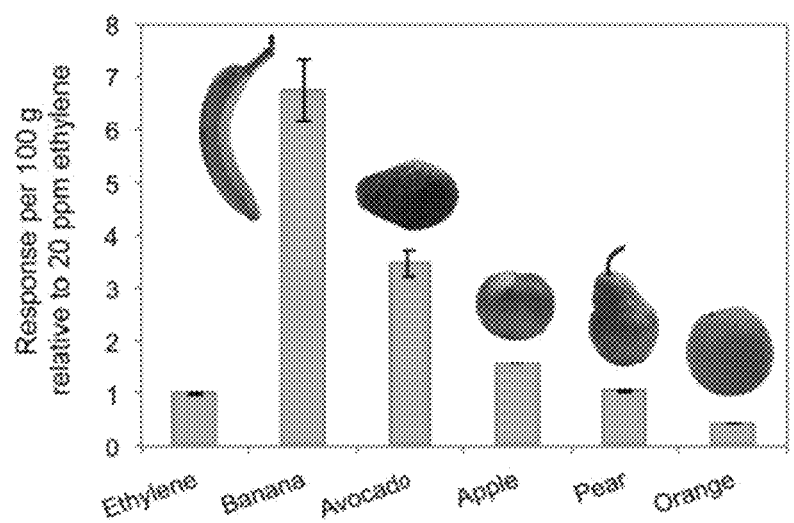
FIG. 6A shows responses of 1-SWCNT devices to 100 g of different fruit relative to 20 ppm ethylene.
Figure 6B:
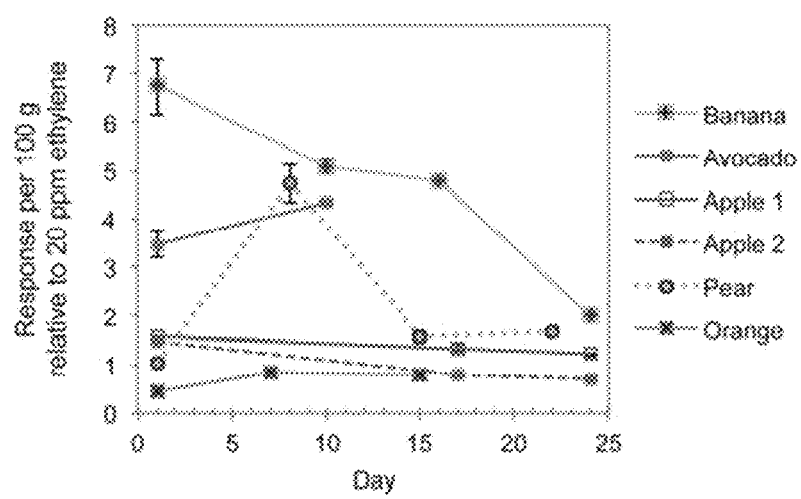
FIG. 6B shows responses to fruit monitored over several weeks.

The system was used to compare the ethylene emission from a selection of common fruits (banana, avocado, apple, pear, and orange). In the experimental setup, the fruit was enclosed in the gas flow chamber as shown in FIG. 2, which allowed exposing the devices to fruit volatiles in the same way as to ethylene. The responses of 1-SWCNT devices to the different fruits are shown in FIG. 6A. The intensities are given in relation to the response to 20 ppm ethylene and normalized to 100 g fruit. The largest responses were found for banana, followed by avocado, apple, pear, and orange. All fruit apart from orange showed ethylene concentrations above 20 ppm, which corresponded to emission rates exceeding 9,600 nL/min. In order to follow the ripening and senescing process in these fruits, their ethylene emission was repeatedly measured over several weeks (FIG. 6B). Fruit can be classified into climacteric and non-climacteric fruit according to respiration rate (release of CO$_2$) and C$_2$H$_4$ production pattern. Banana, avocado, apple, and pear belong to the climacteric group, which is characterized by a large increase in CO$_2$ and C$_2$H$_4$ production during ripening, while non-climacteric fruits, such as orange, generally show low emission rates of these gases. Once the climax (ripeness) is achieved, respiration and C$_2$H$_4$ emission decrease as the fruit senesces. The climacteric rise during ripening was observed in case of the pear and avocado, which showed an increased ethylene emission after the first week. For all other fruits and after the second week for the pear, measurements were conducted close to the maximum point of ripeness, and as a result the data reflects the senescence of the fruit with decreasing ethylene production rates for banana and apple. Two apples of the same kind and of similar ripeness were compared, of which one was stored in a refrigerator (apple 1), while apple 2 was kept at room temperature. As anticipated, apple 2 senesced faster at room temperature, and hence its ethylene production decreased at a quicker pace than for apple 1. The orange as a non-climacteric fruit showed an overall low emission rate of ethylene.

Figure 7:
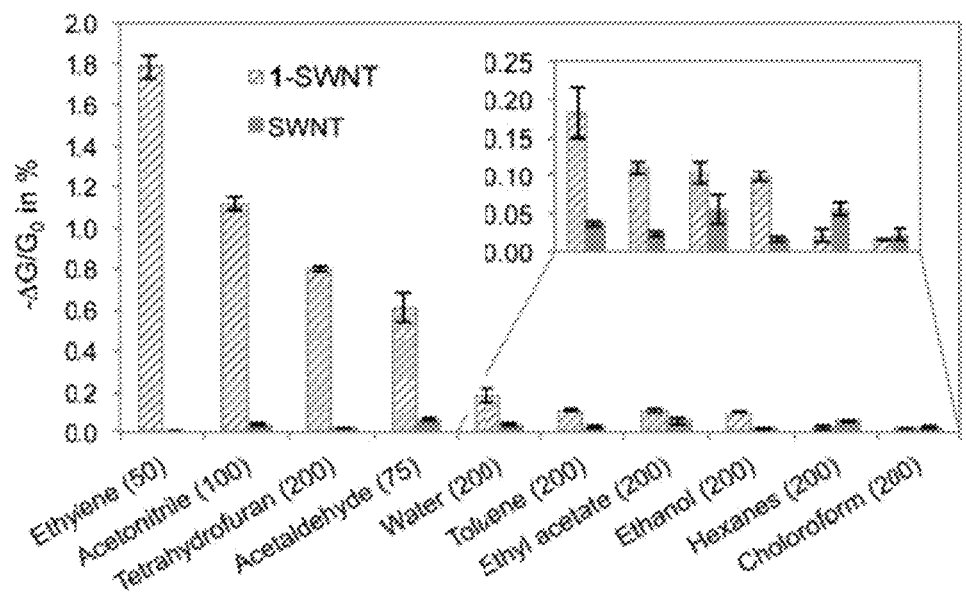
FIG. 7 shows relative responses of 1-SWCNT devices and pristine SWCNT to 50 ppm ethylene and various solvents diluted with nitrogen gas (respective concentrations are given in parentheses in ppm).

In order to assess the selectivity of our sensory system, responses of 1-SWCNT devices to several solvents (75-200 ppm concentrations) as representatives of functional groups were measured, as well as to ethanol and acetaldehyde, which occur as fruit metabolites. The results are shown in FIG. 7 in comparison to the response to 50 ppm ethylene and to pristine SWCNTs.

Significantly high responses were observed towards acetonitrile, THF, and acetaldehyde, while all other solvents had only small effects. However, considering the concentrations of these compounds the responses were smaller in magnitude than the response to ethylene (50 ppm ethylene vs. 100 ppm acetonitrile, 200 ppm THF or 75 ppm acetaldehyde). The sensitivity of 1-SWCNT devices towards these analytes was not surprising, as they are able to bind to the copper center in 1 via the nitrile group (acetonitrile), the ether group (THF), or the oxygen of acetaldehyde.

Figure 8:
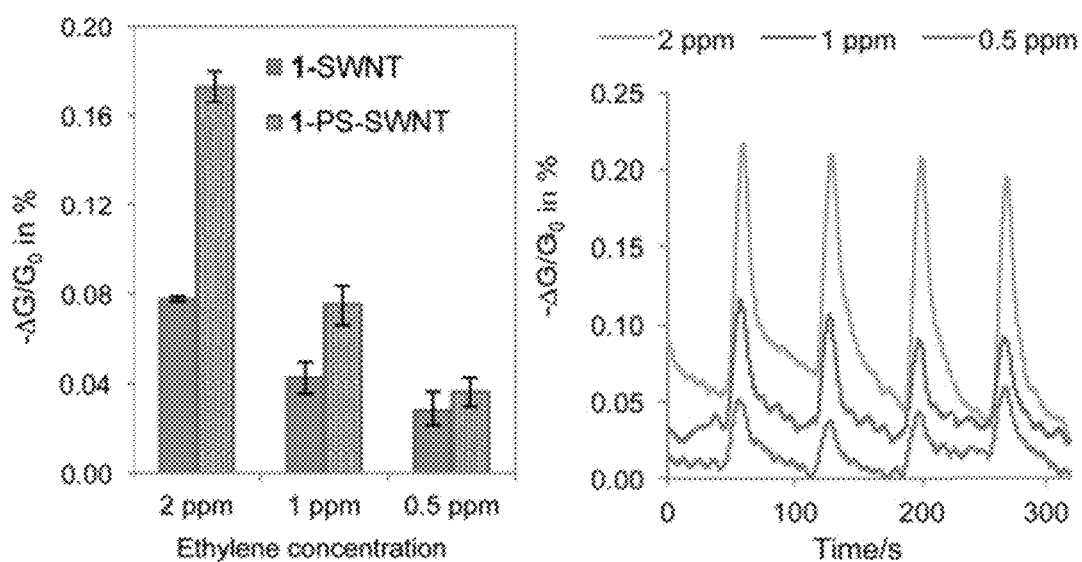
FIG. 8 shows a comparison of the responses of 1-SWCNT devices and 1-PS-SWCNT devices to 0.5, 1, and 2 ppm ethylene.

The concentrations required for fruit ripening lie in most cases between 0.1 and 1 ppm, and hence in storage facilities the ethylene level is to be kept below those thresholds. The sensory system consisting of 1 and SWCNTs showed good responses down to 1 ppm of ethylene. Sensitivity can be improved by increasing the surface area and porosity of the SWCNT network structure. In order to achieve this 5 weight-% cross-linked polystyrene beads of 0.4-0.6 μm diameter was added to the mixture, from which devices were prepared. The responses of the resulting 1-PS-SWCNT devices to ethylene concentrations of 0.5, 1, and 2 ppm are shown in FIG. 8. A 1.3-2.2 fold increase in sensitivity was observed, which was attributed to an increased surface area of the SWCNT network and possibly an increase in the local ethylene concentration in the device by partitioning into the polystyrene beads—in other words, a preconcentration effect.

Materials and Synthetic Manipulations. Synthetic manipulations were carried out under an argon atmosphere using standard Schlenk techniques. $[CF_3SO_3Cu]_2 \cdot C_6H_6$ was purchased from TCI America, hydrotris[3,5-bis(trifluoromethyl)pyrazol-1-yl]borato sodium ($Na[HB(3,5-(CF_3)_2-pz)_3]$) was prepared following a literature procedure (H. V. R. Dias, et al., Inorg. Chem. 1996, 35, 2317-2328, which is incorporated by reference in its entirety). Single-walled carbon nanotubes were purchased from SouthWest Nano Technologies (SWeNT® SG65, SWeNT®SG65-SRX, SWeNT®SG76, and SWeNT® CG100) or from Unidym (HIPCO® Super Purified). Cross-linked polystyrene particles (0.4-0.6 μm diameter) were purchased from Spherotech and transferred from water into toluene. Dry toluene was purchased from J. T. Baker. All other chemicals were purchased from Sigma Aldrich and used as received. NMR spectra were recorded on Bruker Avance-400 spectrometers.

Synthesis of 1. 8 mg (15.9 μmol) $[CF_3SO_3Cu]_2 \cdot C_6H_6$ were dissolved in 3 mL dry, degassed toluene. 17 mg (43.5 μmol) hydrotris[3,5-bis(trifluoromethyl)pyrazol-1-yl]borato sodium ($Na[HB(3,5-(CF_3)_2-pz)_3]$) were added, and the mixture was stirred for 14 h at r.t. The reaction mixture was filtrated through a syringe filter to receive a colorless solution of 1 with a concentration of ~6 μmol/mL (6 mM).

The exact concentration of 1 was determined in the following way: A small amount of the solution was purged with ethylene for 20 min. The solvent was then evaporated, and the concentration of 1 determined by NMR spectroscopy using benzene as a reference for integration.

Preparation of 1-SWCNT. 0.50 mg (41.6 μmol carbon) of SWCNTs were suspended in 0.8 mL dry o-dichlorobenzene, and 1.16 mL (6.9 μmol) of a 6 mM solution of 1 in toluene were added. The mixture was sonicated at 30° C. for 30 min. The resulting black dispersion of 1-SWCNT was used to prepare devices.

Preparation of 1-PS-SWCNT. 0.50 mg (41.6 μmol carbon) of SWCNTs were suspended in 0.8 mL dry o-dichlorobenzene, and 1.16 mL (6.9 μmol) of a 6 mM solution of 1 in toluene as well as 2.4 μL of a suspension of cross-linked polystyrene particles in toluene (5 μg/mL) were added. The mixture was sonicated at 30° C. for 30 min. The resulting black dispersion of 1-PS-SWCNT was used to prepare devices.

Device preparation. Glass slides (VWR Microscope Slides) were cleaned by ultrasonication in acetone for 10 min, and after drying they were subjected to UV radiation in a UVO cleaner (Jelight Company Inc.) for 3 min. Using an aluminum mask, layers of chromium (10 nm) and gold (75 nm) were deposited leaving a 1 mm gap using a metal evaporator purchased from Angstrom Engineering. Volumes of 1 μL of the dispersion of 1-SWCNT was drop-cast in between the gold electrodes followed by drying in vacuum until a resistance of 1-5 kΩ was achieved.

Sensing measurements. Devices were enclosed in a homemade Teflon gas flow chamber for sensing measurement (see FIGS. 2A-2B). The gold electrodes of the device were contacted with connections to the outside of the gas flow chamber, and two ports on opposite sides of the chamber allowed to direct a continuous gas flow through the chamber. The low concentration gas mixtures were produced using a KIN-TEK gas generator system. A trace amount of analyte emitted from a permeation tube is mixed with a nitrogen stream (oven flow), which can be further diluted with nitrogen (dilution flow). For ethylene, refillable permeation tubes were used, while for the solvents calibration measurements were performed by placing the solvent in the oven flow for set amounts of time. For fruit measurements, the fruit was placed in a flow chamber, through which the "oven flow" was directed, which was then further diluted with nitrogen.

Electrochemical measurements were performed using an AUTOLAB instrument from Eco Chemie B.V. A constant bias voltage of 0.1 V was applied across the device, while current vs. time was measured. During the measurement the volume of gas flow over the device was held constant and switched between nitrogen and analyte/nitrogen.

FET Measurements. As a substrate for FET measurements, a piece of silicon with a 300 nm $SiO_2$ insulating layer onto which Au electrodes had been deposited, was chosen. Interdigitated electrodes with a 10 μm gap were used. Analogous to the preparation of the devices for amperometric sensing measurements, dispersions of 1-SWCNT and of pristine SWCNTs were drop-cast between these electrodes. For the measurements, the device was enclosed in a teflon chamber analogous to FIG. 2B with an additional electrode to contact the Si bottom gate. The source-gate potential was swept from +2 V (+5 V in the case of 1-SWCNT) to −20 V at a constant source-drain, bias of 0.1 V and the chamber was flooded with nitrogen during the measurement. The source-drain current as well as the gate leakage current were recorded (FIGS. 9A-9D).

Testing of different SWCNT Types and Control Experiments. While optimizing sensitivity of the devices to ethylene, different types of SWCNTs were tested. In FIG. 10 (left) are shown the relative responses of devices made from different 1-SWCNT dispersions. The results of control experiments, in which dispersions of 2-SWCNT, 4-SWCNT (see below for structure of 4) and SWCNTs with [Cu(CH$_3$CN)$_4$]PF$_6$ were used to prepare devices are shown on the right in FIG. 10.

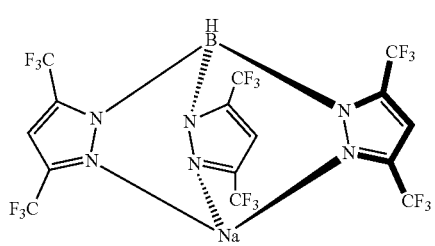

4

Fruit Information. Fruit of the following types and weight was purchased from a Farmer's market: Banana (Cavendish) −142.5 g; Avocado (Hass) −170.7 g; Apple 1 (Macintosh) −119.1 g; Apple 2 (Macintosh) −111.3 g; Pear (Cornice) −246.1 g; Orange (Navel) −265.0 g.

Figure 11B:
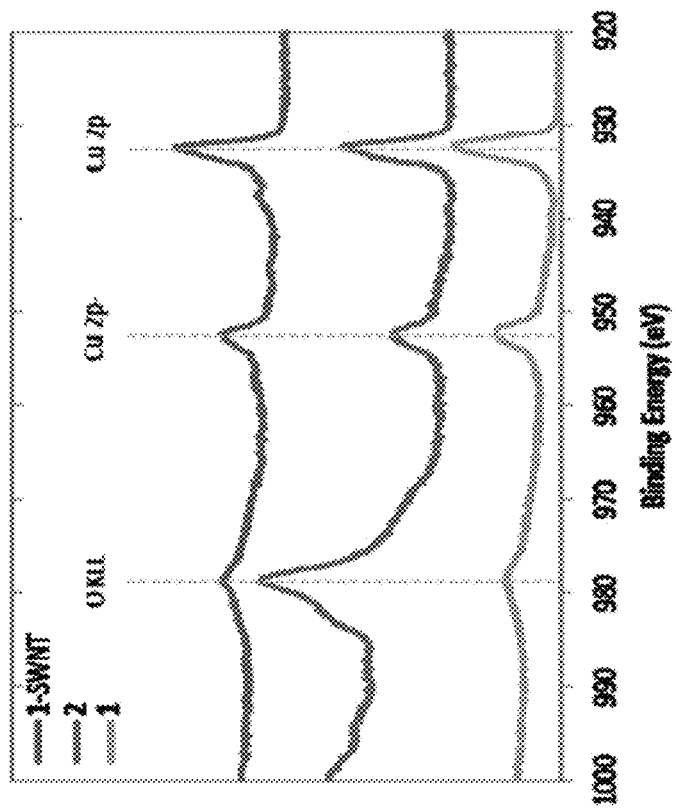
FIGS. 11A-11B show results of XPS measurements.
Figure 11A:
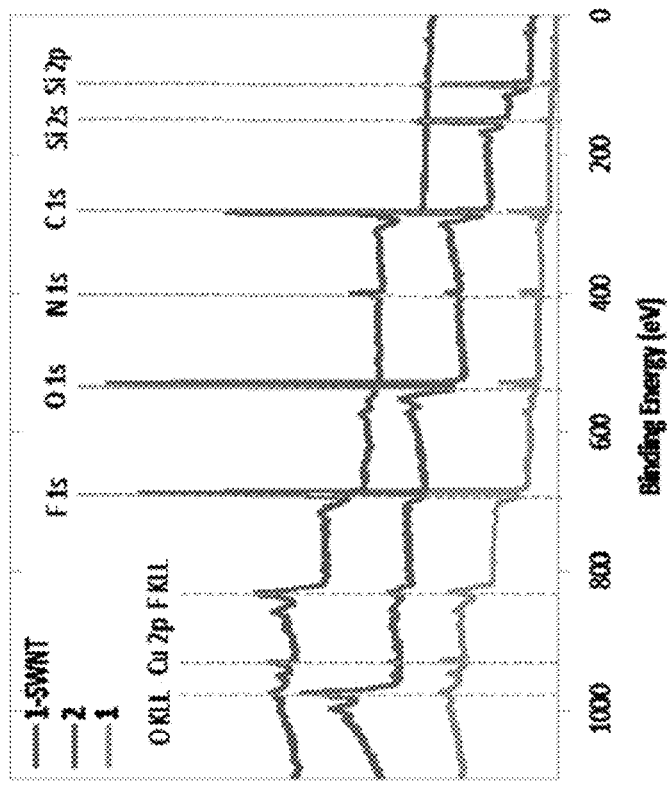

Raman Measurements, IR Measurements, and XPS Data. IR spectra were recorded on a SMART iTR purchased from Thermo Scientific. The sample was dropcast onto a KBr card, and the spectrum measured in transmission mode. Raman spectra were measured on a Horiba LabRAM HR Raman Spectrometer using excitation wavelengths of 785 nm and 532 nm. The samples were dropcast onto SiO$_2$/Si substrates for the measurement. XPS spectra were recorded on a Kratos AXIS Ultra X-ray Photoelectron Spectrometer. The samples were drop-cast onto SiO$_2$/Si substrates for the measurements. As the copper complex 1 is air sensitive, it was drop-cast under argon and the exposure to air was kept minimal (<2 min) during the transfer into the XPS instrument. In the case of 1 and 2 sample charging was observed and a charge neutralizer was used. The resulting shift in energy was compensated by calibrating using the F 1s peak at 687 eV. FIGS. 11A-11B show results of the XPS measurements.

Isodesmic Equation. The isodesmic equation that allows comparing the binding strength of 1 to ethylene or a SWCNT is:

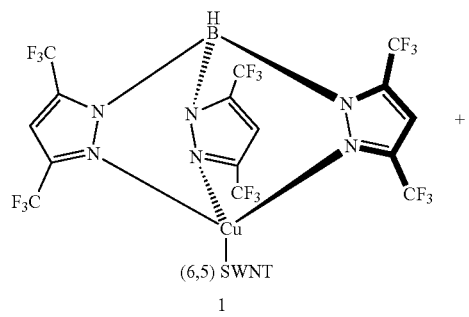

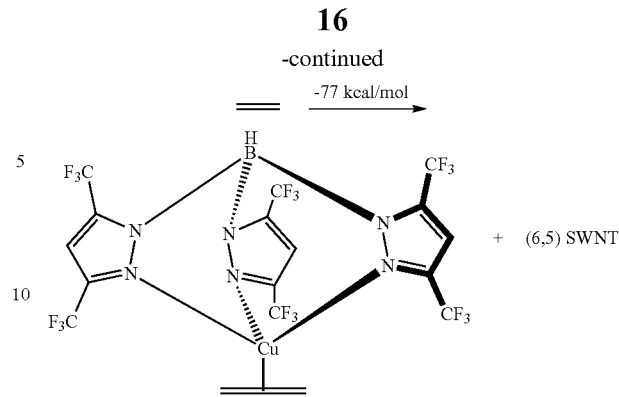

Electronic and zero-point vibrational energies. Electronic energies ($\varepsilon_0$), zero point vibrational energies (ZPVE), total energies (E$_{total}$), and free energies G for all calculated structures (local minima) of the isodesmic equation (B3LYP/6-31G* for C, H, B, F, N, LanL2DZ for Cu) are shown in Table 1.

TABLE 1

| Compound | $\varepsilon_0$ [hartrees] | ZPVE [hartrees] | E$_{total}$ [kcal/mol] |
|---|---|---|---|
| 2 | −3000.31041 | 0.28383 | −1882546.7 |
| 3 | −7126.899656 | — | — |
| Ethylene | −78.58746 | 0.05123 | −49282.3 |
| (6,5) SWCNT fragment | −4205.29893 | 0.92740 | −2638285.2 |

Figure 12:
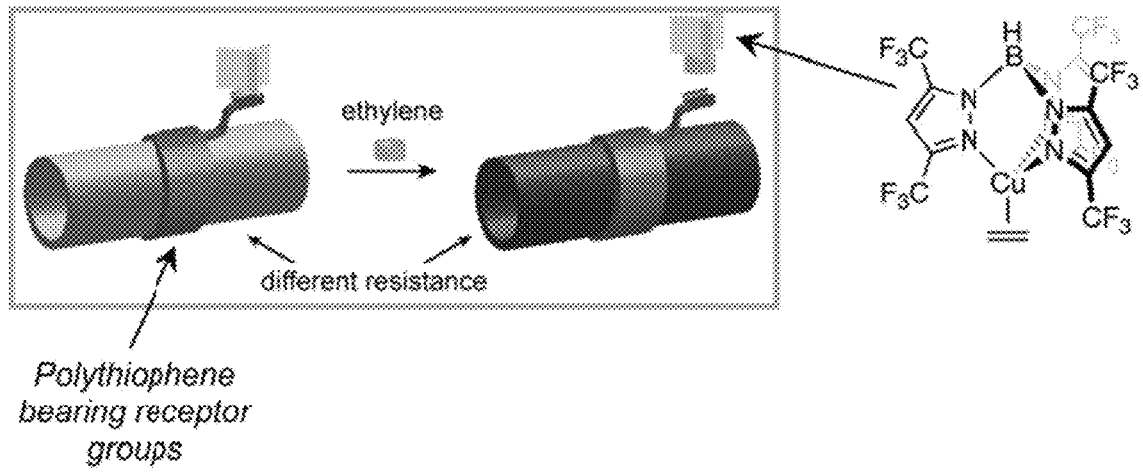
FIG. 12 is a schematic illustration of ethylene sensing using polymer-wrapped SWCNTs.

Polymer-wrapped SWCNTS. FIG. 12 illustrates a polythiophene-wrapped SWCNT having pendant groups that bind to a transition metal complex. When exposed to an analyte, e.g., ethylene, the analyte binds to the transition metal complex, displacing it from the pendant group. The SWCNT has differing resistances in these two states.

Polythiophenes for wrapping SWCNTs, PT1, PT2, PT3, and PT4, are shown below:

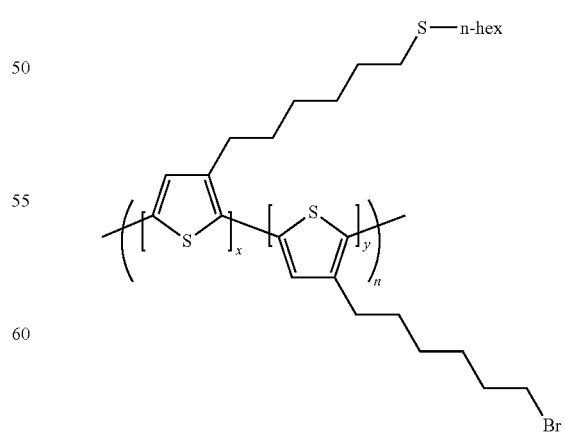

PT1: x/y = 1.3
PT2: x/y = 6.5

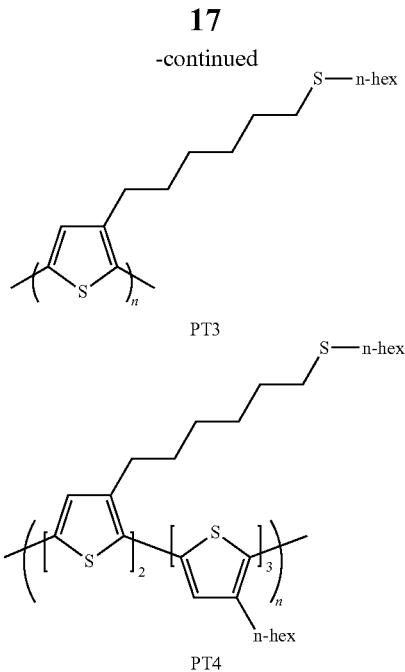

PT3

PT4

Polymer-wrapped SWCNTs were prepared by combining a polythiophene (PT) with SWCNT in $CHCl_3$ and sonicating. The mixture was centrifuged and the supernatant isolated; material was then precipitated with ethanol, providing polythiopene-wrapped SWCNT (PT/SWCNT). These were suspended in $CHCl_3$ and a solution of copper complex 1 in toluene was added, affording PT/SWCNT/1 complexes. These were spin coated over gold electrodes for measurements.

Figure 13:
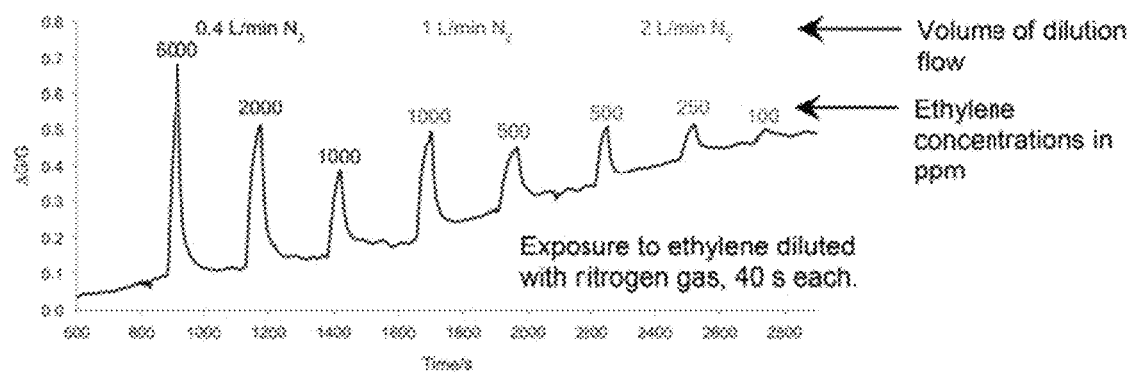
FIG. 13 shows the response of a PT1/SWCNT/1 device to ethylene.

FIG. 13 shows relative responses of a PT1/SWCNT/1 device to low concentrations of ethylene. Reversible responses to low concentrations of ethylene were observed, with sensitivity down to 100 ppm of ethylene. PT1/SWCNT devices without any transition metal complex showed no response even to 6000 ppm ethylene.

Figure 14:
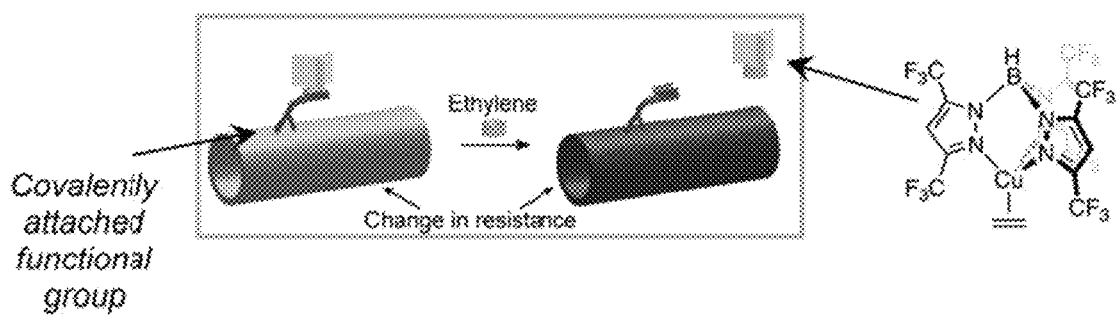
FIG. 14 is a schematic illustration of ethylene sensing using covalently modified SWCNTs.

Covalently modified SWCNTs. FIG. 14 illustrates a covalently modified SWCNT having functional groups that bind to a transition metal complex. When exposed to an analyte, e.g., ethylene, the analyte binds to the transition metal complex, displacing it from the functional group. The SWCNT has differing resistances in these two states.

Figure 15:
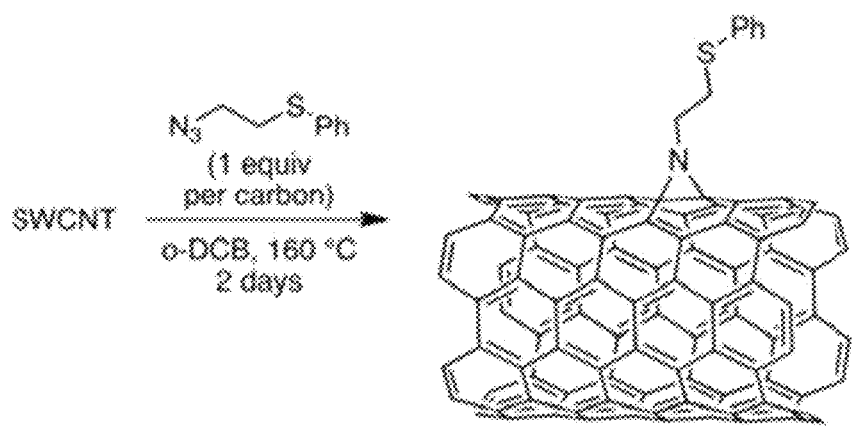
FIG. 15 is a schematic illustration of covalent modification of SWCNTs.
Figure 16:
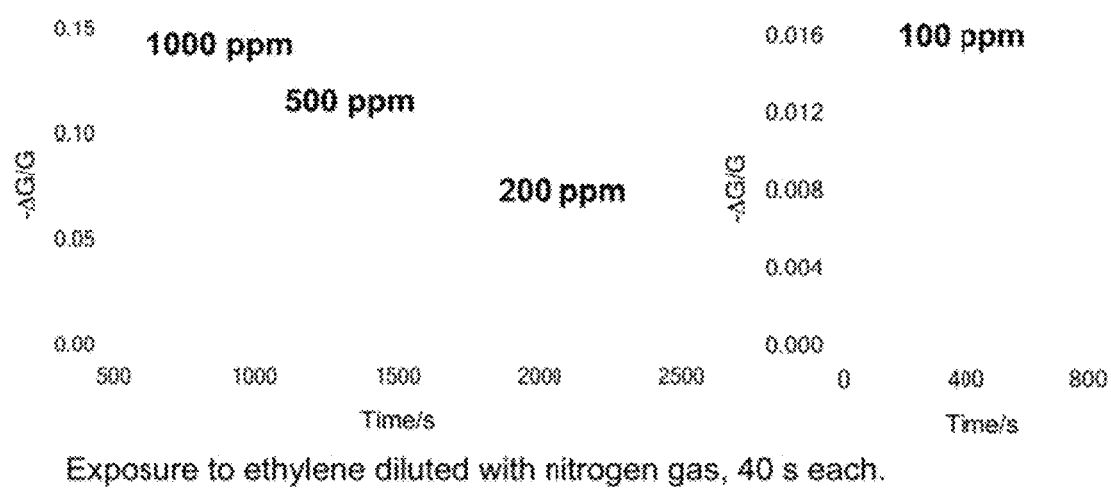
FIG. 16 shows the response of a device having covalently modified SWCNTs to ethylene.

FIG. 15 illustrates the functionalization of SWCNTs: SWCNTs were combined with S-(2-azidoethyl)thiophenol (1 equiv. per carbon) in o-dichlorobenzene at 160° C. for 2 days to provide modified SWCNTs. Devices were prepared by combining modified SWCNTs and 1 in o-dichlorobenzene and sonicating, then dropcasting the resulting complexes between gold electrodes. FIG. 16 shows relative responses of such a device to low concentrations of ethylene. Reversible responses to low concentrations of ethylene were observed, with sensitivity to less than 100 ppm of ethylene.

Ethylene Sensors by Abrasion

Preparation of a 1-SWCNT pellet. 94 mg (0.187 mmol) $[CF_3SO_3Cu]_2 \cdot C_6H_6$ were dissolved in 30 mL dry, degassed toluene. 200 mg (0.311 mmol) hydrotris[3,5-bis(trifluoromethyl)pyrazol-1-yl]borato sodium ($Na[HB(3,5-(CF_3)_2-pz)_3]$) were added, and the mixture was stirred for 15 h at r.t. The reaction mixture was filtered under argon to yield a colorless solution of I with a concentration of ~13 mol/mL (13 mM), as determined by NMR. 31.7 mg (2.64 mmol carbon) of SWCNTs were added to the solution, and the resulting mixture was sonicated at 30° C. for 30 min under argon. The resulting black dispersion was evaporated to dryness in vacuo yielding 207 mg of a black powder.

Preparation of a 2-SWCNT pellet. 370 mg (0.70 mmol) $[CF_3SO_3Cu]_2 \cdot C_6H_6$ were dissolved in 38 mL dry, degassed toluene. 1 g (1.55 mmol) hydrotris[3,5-bis(trifluoromethyl)pyrazol-1-yl]borato sodium ($Na[HB(3,5-(CF_3)_2-pz)_3]$) were added, and the mixture was stirred for 17 h at r.t. Subsequently, ethylene was bubbled through the solution for 40 min. The solution was then stirred for 4 h in an ethylene atmosphere at r.t. Solids were removed by filtration through a glass frit and solvent was removed from the resulting solution. 497 mg (0.7 mmol) of 2 were obtained as a white powder. 125 mg of 2 were mixed with 25 mg SWCNTs by ball-milling yielding a black powder.

Sensor fabrication by drawing and sensing measurement. The black powder of 1+SWCNT or 2+SWCNT was subsequently compressed into a pellet and sensors were fabricated by drawing with the pellet between two gold electrodes on paper. Sensing measurements were performed as described above. The complex formed with ethylene is represented below.

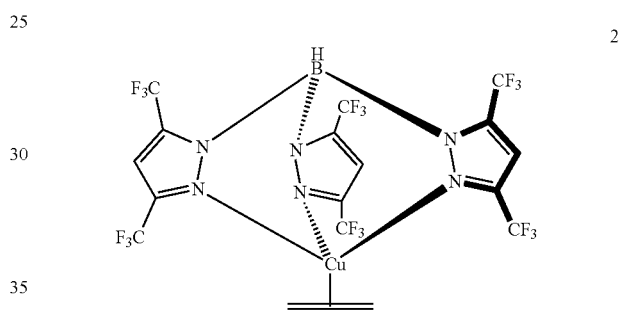

2

Figure 17:
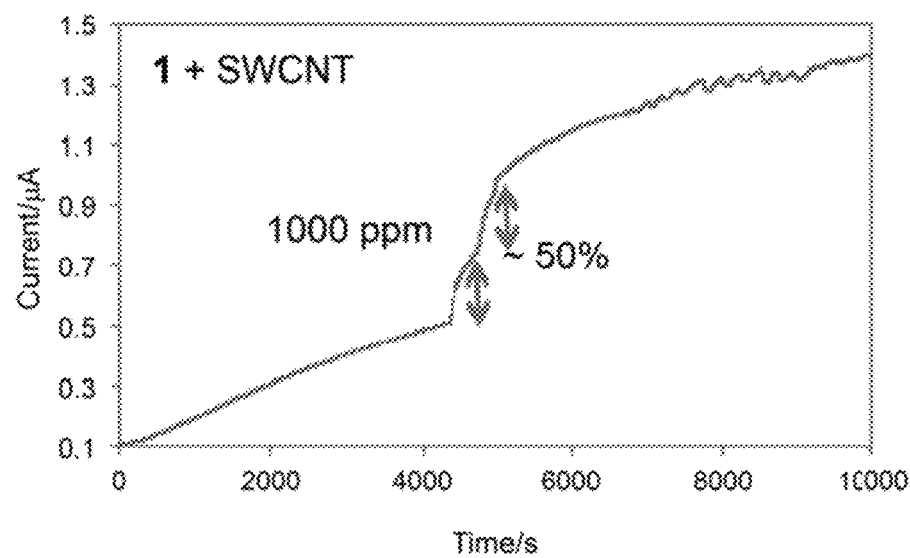
FIG. 17 is a graph showing the response of sensor fabricated by drawing with a pellet of Cu(I) scorpionate ethylene complex 2 and SWCNTs to ethylene.
Figure 18:
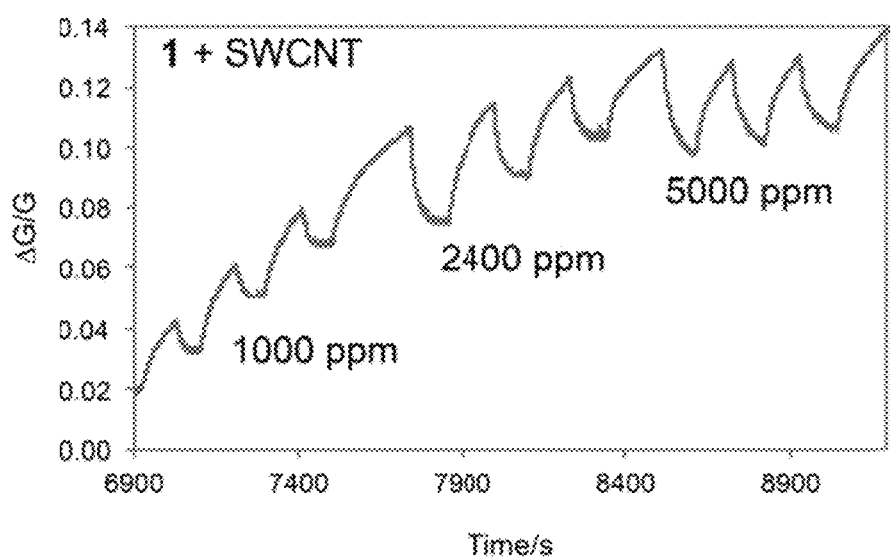
FIG. 18 is a graph showing the response of sensor fabricated by drawing with a pellet of Cu(I) scorpionate ethylene complex 2 and SWCNTs to ethylene.
Figure 19:
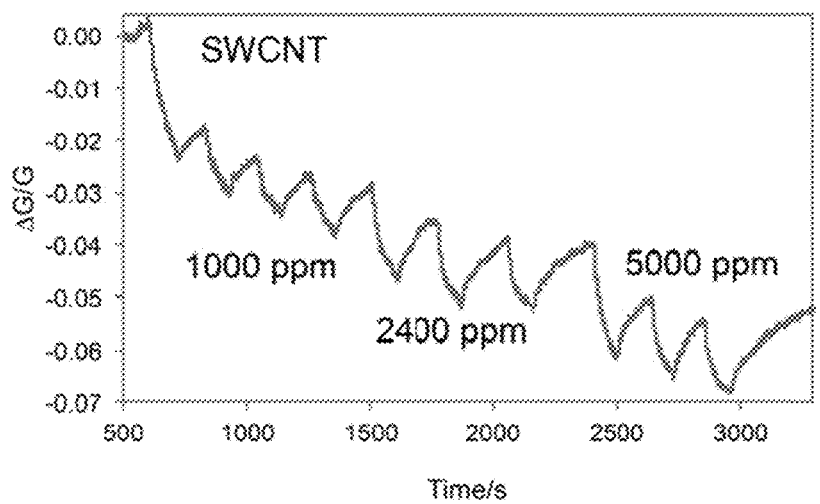
FIG. 19 is a graph showing the response of sensor fabricated by drawing with a pellet of SWCNTs to ethylene.
Figure 20:
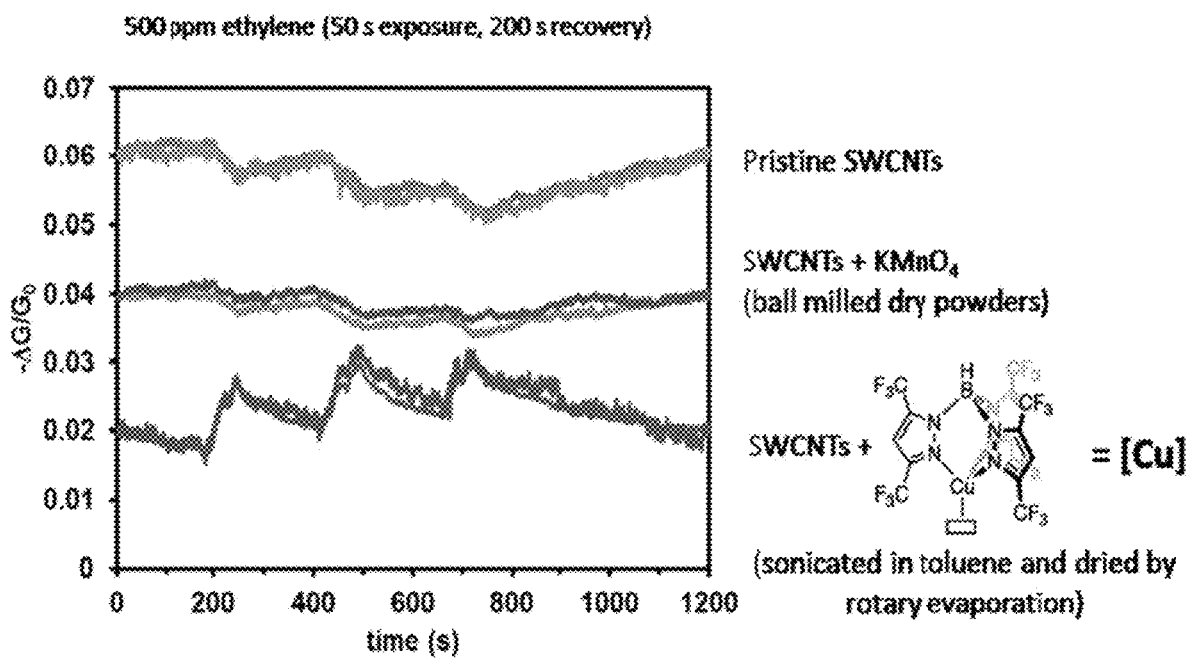
FIG. 20 is a graph showing the sensing response of devices fabricated by abrasion with pristine SWCNTs, SWCNTs+$KMnO_4$ and SWCNTs+1 on HP multipurpose paper to 500 ppm 5 ethylene.
Figure 21:
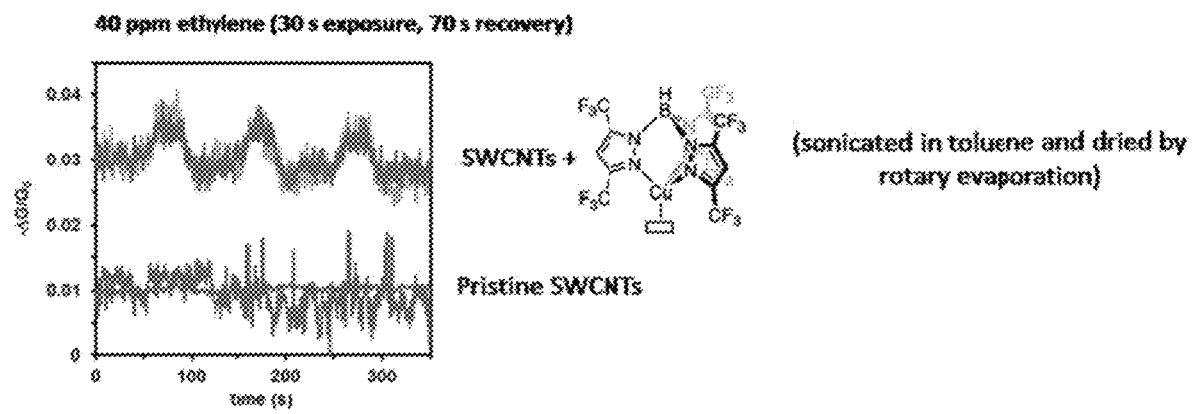
FIG. 21 is a graph showing the sensing response of devices fabricated by abrasion with SWCNTs+1 and pristine SWCNTs on the surface of weighing paper to 40 ppm ethylene.

The response of sensor fabricated by drawing with a pellet of Cu(I) scorpionate 2 and SWCNTs to ethylene can be seen at FIGS. 17-19. The sensing response of devices fabricated by abrasion with pristine SWCNTs, SWCNTs+$KMnO_4$ and SWCNTs+1 on HP multipurpose paper to 500 ppm ethylene can be seen at FIG. 20. The sensing response of devices fabricated by abrasion with SWCNTs+1 and pristine SWCNTs on the surface of weighing paper to 40 ppm ethylene can be seen at FIG. 21.

Generation of Sensing Material Via Spray-Drying

Spray-drying of a mixture of 1 and SWCNTs can potentially lead to better mixing of both components and thus potentially a higher sensing performance. This is most relevant for the abrasion fabrication method above.

Material preparation. SWCNTs were suspended in dry o-dichlorobenzene (1.6 mL per mg of SWCNTs), and ⅙ equivalents of 1 in toluene were added to obtain a suspension containing 0.3 wt % total solid material in 1:1 o-dichlorobenzene/toluene. The mixture was sonicated at 30° C. for 30 min. The resulting black suspension was subjected to spray-drying at a nozzle temperature of 210° C. in a nitrogen atmosphere. A highly viscous product was obtained.

Device preparation. Gold (100 nm) was deposited onto pieces of paper using a shadow mask in a metal evaporator purchased from Angstrom Engineering. The resulting devices contained 9 separate working electrodes and one shared counter electrode at a gap size of 1 mm. The previously obtained material containing 1-SWCNT as well as residual solvent was applied to the gap of the device using a spatula.

Figure 22:
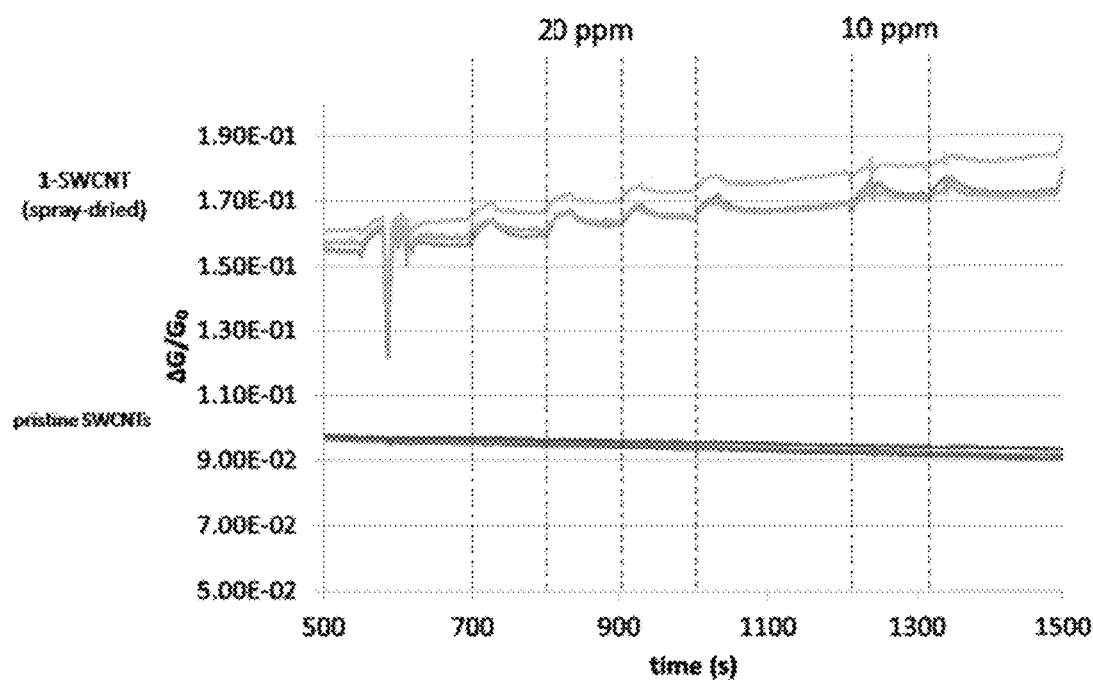
FIG. 22 is a graph showing the sensing response of devices based on 1-SWCNTs (spray dried) and pristine SWCNTs to 20 ppm and 10 ppm ethylene. Dashed lines indicated the time at 10 which the exposure was started. Devices were exposed to ethylene for 30 sec each.

Sensing Measurements. The device was enclosed in a homemade Teflon gas flow chamber and connected to an array potentiostat via an edge connector and breadboard. A continuous flow of gas was applied to the device in the chamber using a KIN-TEK gas generator system. A trace amount of analyte emitted from a permeation tube is mixed with a nitrogen stream (oven flow), which can be further diluted with nitrogen (dilution flow). For ethylene, refillable permeation tubes were used. A graph of the measurements can be seen at FIG. 22.

Polymer Coating of Sensor Devices, Composites

The current lifetime of our ethylene sensors is currently ca. 2 weeks and we would like to increase it. Furthermore, some coatings could "shield" the sensor from moisture while being permeable to ethylene. Lastly, coatings could have a preconcentrator effect.

Polymer coated devices as described below have been prepared and tested. However, a response to ethylene with that type of setup has not been achieved due to technical difficulties. Preparation of polymer coated devices:

Device preparation. Glass slides (VWR Microscope Slides) were cleaned by ultrasonication in acetone for 10 min, and after drying they were subjected to UV radiation in a 15 UVO cleaner (Jelight Company Inc.) for 3 min. Using a stainless steel shadow mask, layers of chromium (10 nm) and gold (100 nm) were deposited resulting in 14 working electrodes and I shared counter electrode with a 1 mm gap using a metal evaporator purchased from Angstrom Engineering. Volumes of 1 μL of the dispersion of 1-SWCNT was drop-cast in between the gold electrodes followed by drying in vacuum until a resistance of 1-5 kΩ was achieved.

A solution of a polymer in dichloromethane was prepared by adding 10 mg of the polymer to 1 mL of DCM, followed by sonication. 2 times 1 μL of the solution was drop-cast onto the 1-SWCNT material of the sensor. Two devices each were prepared with the following polymers: polyethylene, polystyrene, poly(ethylene oxide), polyvinylidene fluoride, Nafion, and Poly[2-methoxy-5-(2-ethylhexyloxy)-1,4-phenylenevinylene].

Figure 23:
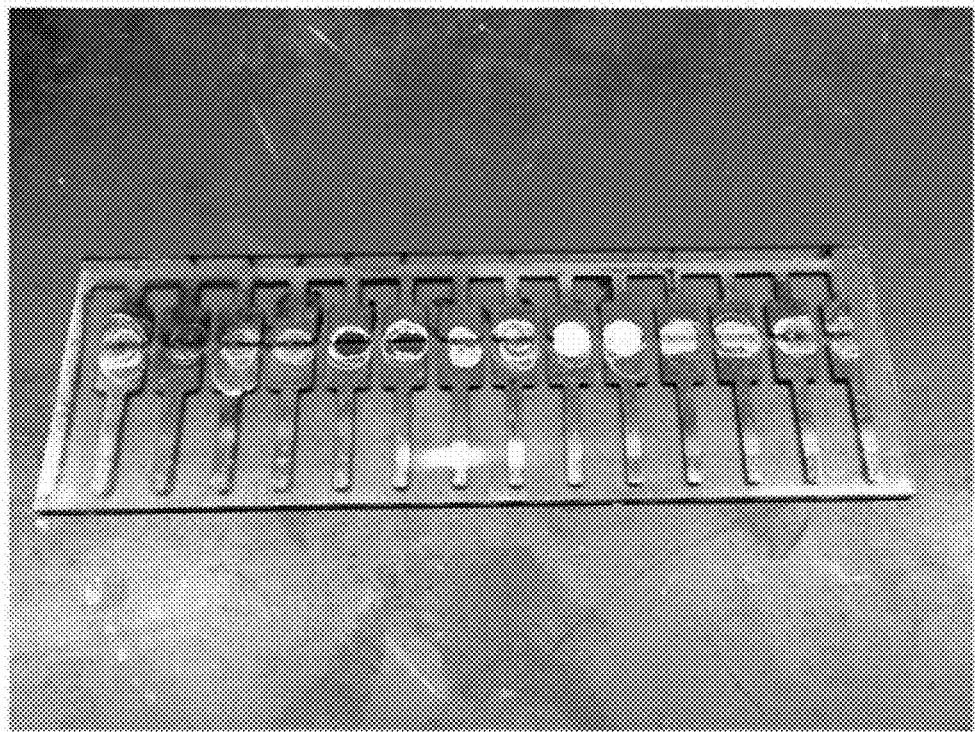
FIG. 23 is a photograph of a glass slide with 14 devices that were coated with different polymers.

Sensing Measurement. Subsequently, the glass slide with 14 devices was enclosed in a homemade Teflon gas flow chamber and connected to an array potentiostat via an edge connector and breadboard. See FIG. 23. A continuous flow of gas was applied to the device in the chamber using a KIN-TEK gas generator system. A trace amount of analyte emitted from a permeation tube is mixed with a nitrogen stream (oven flow), which can be further diluted with nitrogen (dilution flow). For ethylene, refillable permeation tubes were used.

Array Sensors

Combining different sensors into a sensor array can have several advantages. Reproducibility can be improved by signal averaging over several sensors of the same type, lifetime can be improved by creating additional redundancies, i.e. if one sensor fails, other sensors can still work. Additionally, sensors of different types can be combined to improve selectivity of the sensor. For this goal, ethylene sensors that use different sensing materials can be combined. The different materials will likely lead to different reaction to interferents. Also, sensors that are designed specifically to react with interferents (e.g. water, alcohols, aldehydes, ketones, esters, hydrocarbons etc.) can be included to correctly observe the response to these analytes and thus avoid false positives.

Material Preparation.

Ball-Milling: SWCNTs were mixed with a selector, such as Ag(OTf) or Pd(OCOCF$_3$)$_2$ at a weight ratio of 5:1 selector to SWCNT and subjected to ball milling. The obtained material was compressed into a pellet.

Spray-Drying: SWCNTs were mixed with a selector, such as Ag(OTf) or Pd(OCOCF$_3$)$_2$. 100 mL toluene were added and the mixture was sonicated for 5 minutes as well as throughout the spray-drying process. The suspension was spray-dried at a nozzle temperature of 180° C. in a nitrogen atmosphere yielding a black powder. The powder was compressed into a pellet.

To obtain 1-SWCNT, SWCNTs were suspended in dry o-dichlorobenzene (1.6 mL per mg of SWCNTs), and ⅙ equivalents of 1 in toluene were added to obtain a suspension containing 0.3 wt % total solid material in 1:1 o-dichlorobenzene/toluene. The mixture was sonicated at 30° C. for 30 min. The resulting black suspension was subjected to spray-drying at a nozzle temperature of 210° C. in a nitrogen atmosphere. A highly viscous product was obtained.

Device preparation. Gold (100 nm) was deposited onto pieces of paper using a shadow mask in a metal evaporator purchased from Angstrom Engineering. The resulting devices contained 9 separate working electrodes and one shared counter electrode at a gap size of 1 mm. The material containing 1-SWCNT as well as residual solvent was applied to the gap of the device using a spatula. Other materials were applied to the substrate by abrasion of the respective material pellet.

Figure 24:
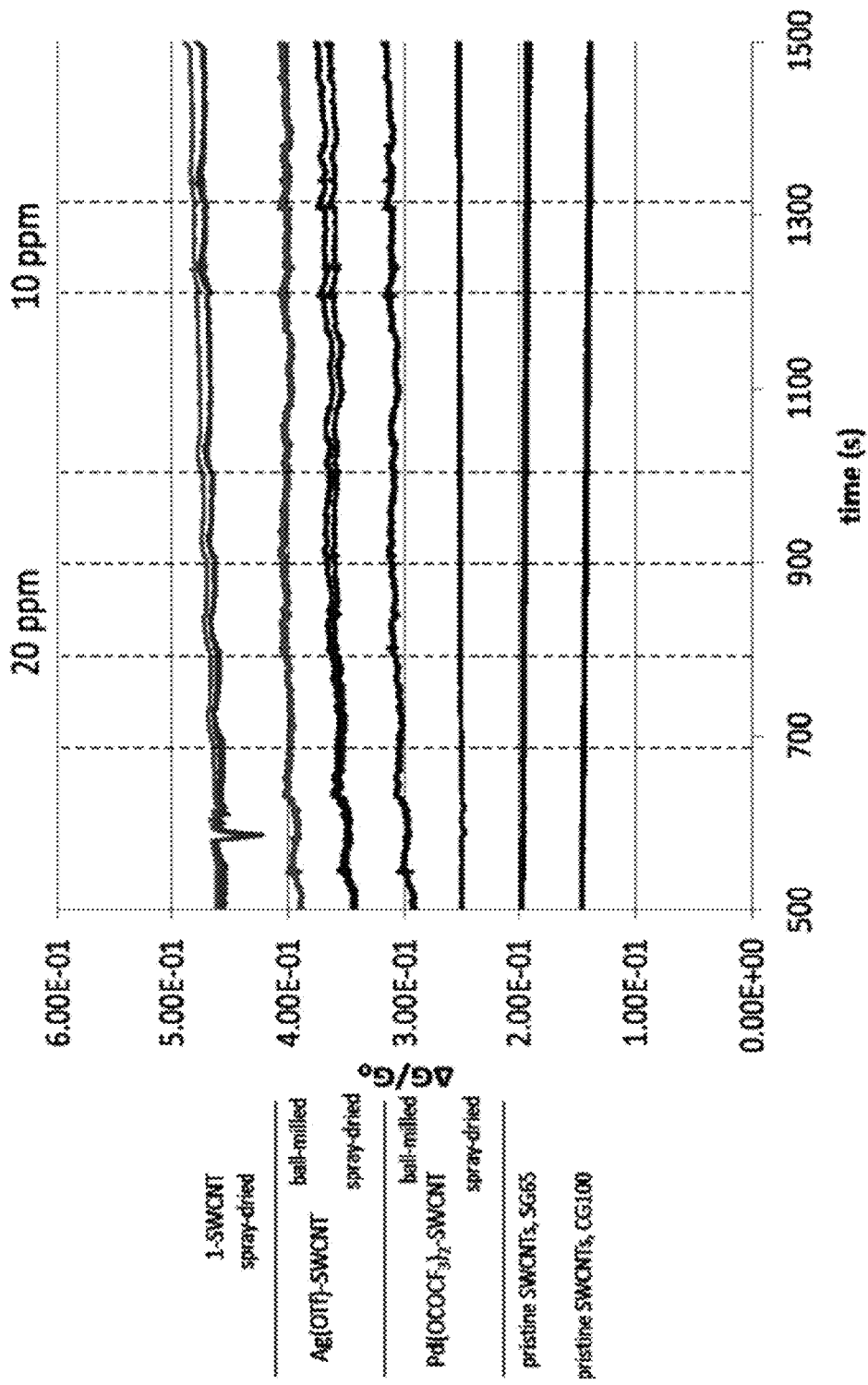
FIG. 24 is a graph showing the sensing response of devices based on 1-SWCNTs (spray dried), Ag(OTf)-SWCNT, $Pd(OCOCF_3)_2$-SWCNTs and two different types of pristine SWCNTs to 20 ppm and 10 ppm ethylene. Dashed lines indicated the time at which the exposure was started. Devices were exposed to ethylene for 30 sec each.
Figure 25:
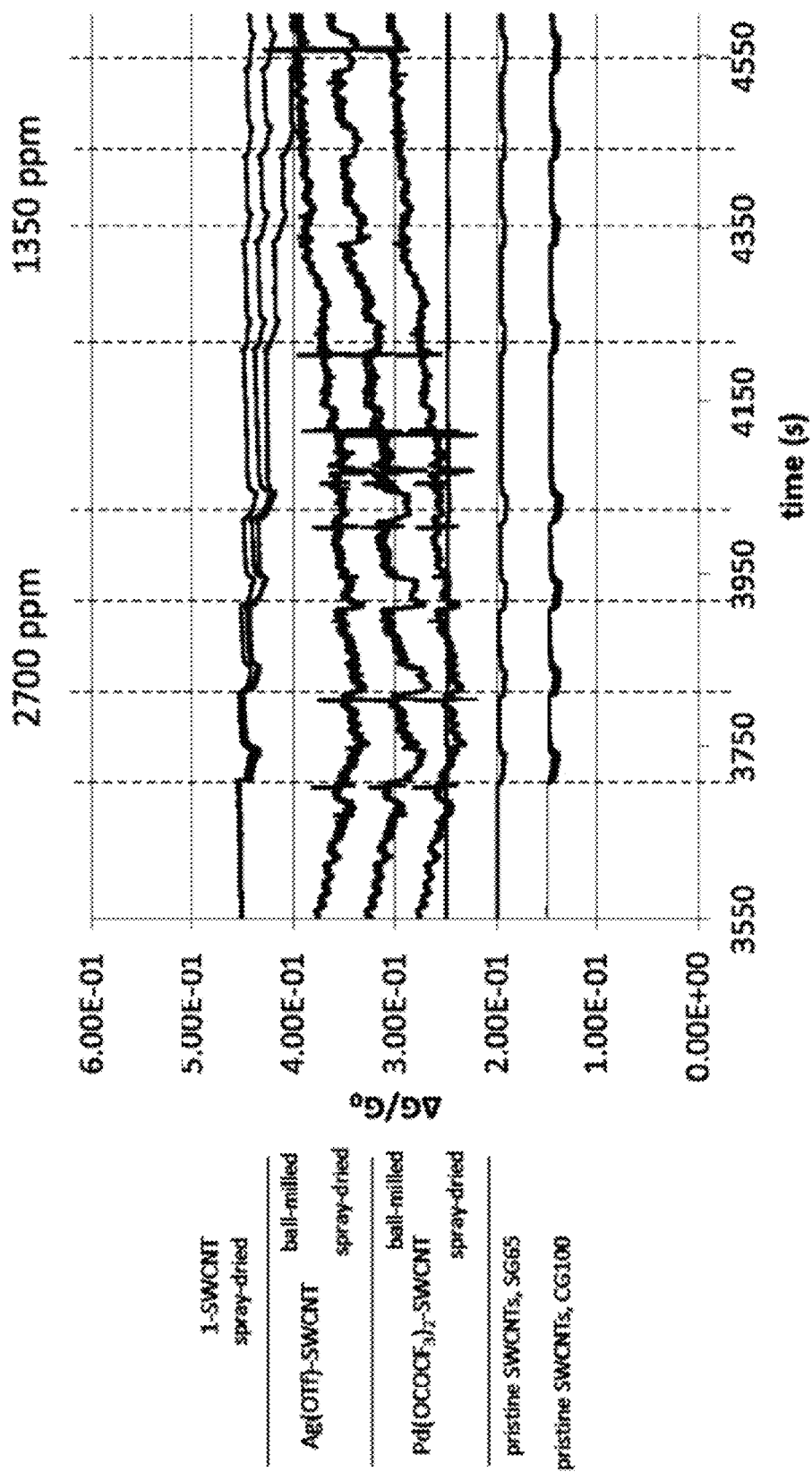
FIG. 25 is a graph showing the sensing response of devices based on 1-SWCNTs (spray dried), Ag(OTf)-SWCNT, $Pd(OCOCF_3)_2$-SWCNTs and two different types of pristine SWCNTs to 2700 ppm and 1350 ppm tetrahydrofuran. Dashed lines indicated the time at which the exposure was started. Devices were exposed to ethylene for 30 sec each.

Sensing Measurement. Subsequently, the devices were enclosed in a homemade Teflon gas flow chamber and connected to an array potentiostat via an edge connector and breadboard. A continuous flow of gas was applied to the device in the chamber using a KIN-TEK gas generator system. A trace amount of analyte emitted from a permeation tube is mixed with a nitrogen stream (oven flow), which can be further diluted with nitrogen (dilution flow). For ethylene, refillable permeation tubes were used. Under the investigated conditions, 1-SWCNT based sensors showed a response to ethylene while the other materials did not show a response (FIG. 24). THF on the other hand led to a response of all sensors in the array (FIG. 25).

Thus, while a single 1-SWCNT based sensor might not be able to distinguish the two analytes, the presented array allows this distinction.

Other embodiments are within the scope of the following claims.

What is claimed is:

1. A sensor comprising:
   a conductive material including a carbon nanotube, the conductive material being in electrical communication with at least two electrodes;
   a transition metal complex including a transition metal, a multidentate ligand, and a ligand including a thiol coordinated to the transition metal and associated with the carbon nanotube, the transition metal complex being mixed with the conductive material, the transition metal complex capable of forming a stable complex with ethylene and interacting with the carbon nanotube and the conductive material via the ligand including the thiol, and
   the at least two electrodes being configured to measure an electrical property between the at least two electrodes in an analyte-free state such that an interaction between the transition metal complex and an analyte results in a change of the measurable electrical property when the sensor is exposed to the analyte.

2. The sensor of claim 1, wherein the transition metal complex is non-covalently associated with the carbon nanotube via the ligand including the thiol.

3. The sensor of claim 1, wherein the transition metal complex is bound to the carbon nanotube of the conductive material.

4. The sensor of claim 1, wherein the transition metal complex has formula (I):

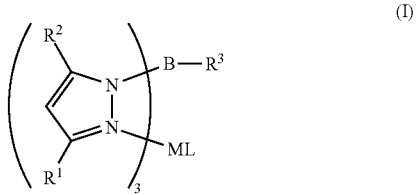
(I)

wherein:
M is a transition metal;
each $R^1$, independently, is H, halo, alkyl, or haloalkyl;
each $R^2$, independently, is H, halo, alkyl, haloalkyl, or aryl;
$R^3$ is H or alkyl; and
L represents the ligand including the thiol;
or the transition metal complex has formula (II):

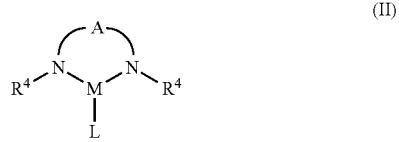
(II)

wherein:
M is a transition metal;
each $R^4$, independently, is alkyl, haloalkyl, aryl, or trialkylsilyl;
A is —CH($R^5$)—X—CH($R^5$)— wherein X is N or CH, and each $R^5$, independently, is H, halo, alkyl, or haloalkyl; or A is —P($R^6$)$_2$—, wherein each $R^6$, independently, is alkyl; and
L represents the ligand including the thiol.

5. The sensor of claim 4, wherein the transition metal complex has the formula:

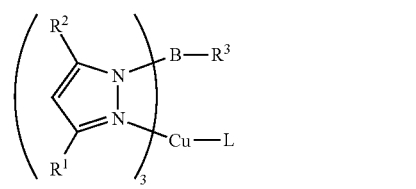

wherein:
each $R^1$, independently, is H, methyl, or trifluoromethyl;
each $R^2$, independently, is H, methyl, trifluoromethyl, or phenyl;
$R^3$ is H or methyl; and
L is the ligand including the thiol.

6. The sensor of claim 1, wherein the transition metal complex and the carbon nanotube are mixed with a polymer.

7. The sensor of claim 6, wherein the polymer is a polymer bead.

8. A sensor comprising:
a carbon nanotube in electrical communication with at least two electrodes; and
a transition metal complex including a transition metal, a multidentate ligand, and a ligand including a thiol coordinated to the transition metal and associated with the carbon nanotube, the transition metal complex capable of forming a stable complex with ethylene and interacting with the carbon nanotube,
the sensor having a baseline level of a measurable electrical property measured between the at least two electrodes in an analyte-free state such that an interaction between the transition metal complex and an analyte results in a change of the measurable electrical property, the transition metal complex associated with the carbon nanotube by a covalent link between the carbon nanotube and the ligand including the thiol.

9. The sensor of claim 8, wherein the transition metal complex has formula (I):

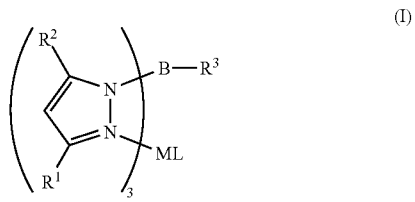
(I)

wherein:
M is a transition metal;
each $R^1$, independently, is H, halo, alkyl, or haloalkyl;
each $R^2$, independently, is H, halo, alkyl, haloalkyl, or aryl;
$R^3$ is H or alkyl; and
L represents the ligand including the thiol;
or the transition metal complex has formula (II):

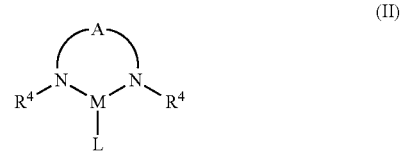
(II)

wherein:
M is a transition metal;
each $R^4$, independently, is alkyl, haloalkyl, aryl, or trialkylsilyl;
A is —CH($R^5$)—X—CH($R^5$)— wherein X is N or CH, and each $R^5$, independently, is H, halo, alkyl, or haloalkyl; or A is —P($R^6$)$_2$—, wherein each $R^6$, independently, is alkyl; and
L represents the ligand including the thiol.

10. The sensor of claim 9, wherein the transition metal complex has the formula:

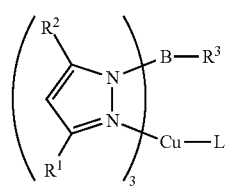

wherein:
  each $R^1$, independently, is H, methyl, or trifluoromethyl;
  each $R^2$, independently, is H, methyl, trifluoromethyl, or phenyl;
  $R^3$ is H or methyl; and
  L is the ligand including the thiol.

11. The sensor of claim 8, wherein the transition metal complex and the carbon nanotube are mixed with a polymer bead.

12. A sensor comprising:
  a carbon nanotube in electrical communication with at least two electrodes; and
  a transition metal complex including a transition metal, a multidentate ligand, and a ligand including a thiol coordinated to the transition metal and associated with the carbon nanotube, the transition metal complex capable of forming a stable complex with ethylene and interacting with the carbon nanotube,
  the sensor having a baseline level of a measurable electrical property measured between the at least two electrodes in an analyte-free state such that an interaction between the transition metal complex and an analyte results in a change of the measurable electrical property, the transition metal complex associated with the carbon nanotube via the ligand including the thiol bound to a polymer which is non-covalently associated with the carbon nanotube.

13. The sensor of claim 12, wherein the transition metal complex has formula (I):

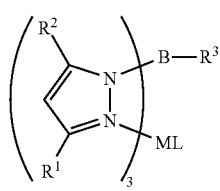

(I)

wherein:
  M is a transition metal;
  each $R^1$, independently, is H, halo, alkyl, or haloalkyl;
  each $R^2$, independently, is H, halo, alkyl, haloalkyl, or aryl;
  $R^3$ is H or alkyl; and
  L represents the ligand including the thiol;
  or the transition metal complex has formula (II):

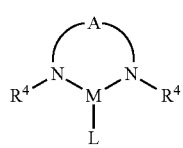

(II)

wherein:
  M is a transition metal;
  each $R^4$, independently, is alkyl, haloalkyl, aryl, or trialkylsilyl;
  A is —CH($R^5$)—X—CH($R^5$)— wherein X is N or CH, and each $R^5$, independently, is H, halo, alkyl, or haloalkyl; or A is —P($R^6$)$_2$—, wherein each $R^6$, independently, is alkyl; and
  L represents the ligand including the thiol.

14. The sensor of claim 13, wherein the transition metal complex has the formula:

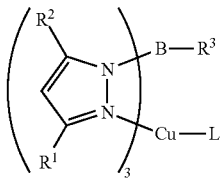

wherein:
  each $R^1$, independently, is H, methyl, or trifluoromethyl;
  each $R^2$, independently, is H, methyl, trifluoromethyl, or phenyl;
  $R^3$ is H or methyl; and
  L is the ligand including the thiol.

15. The sensor of claim 12, wherein the transition metal complex and the carbon nanotube are mixed with a polymer bead.

16. A method of sensing an analyte, comprising:
  exposing a sensor to a sample, the sensor including:
  at least two electrodes;
  a conductive material comprising a carbon-carbon multiple bond moiety, the conductive material being in electrical communication with the at least two electrodes; and
  a transition metal complex including a transition metal, a multidentate ligand, and a ligand including a thiol coordinated to the transition metal the transition metal complex associated with the carbon-carbon multiple bond moiety via the ligand including the thiol, the transition metal complex capable of forming a stable complex with ethylene; and
  measuring an electrical property at the at least two electrodes of the sensor when exposed to an analyte.

17. The method of claim 16, wherein the sample is a gas.

18. The method of claim 16, wherein the analyte is ethylene.

19. The method of claim 16, wherein the transition metal complex has formula (I):

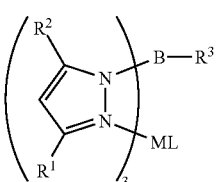

(I)

wherein:
  M is a transition metal;
  each $R^1$, independently, is H, halo, alkyl, or haloalkyl;
  each $R^2$, independently, is H, halo, alkyl, haloalkyl, or aryl;
  $R^3$ is H or alkyl; and
  L represents the ligand including the thiol;

or the transition metal complex has formula (II):

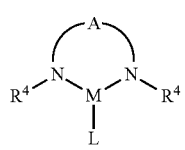

(II)

wherein:
M is a transition metal;
each $R^4$, independently, is alkyl, haloalkyl, aryl, or trialkylsilyl;
A is —CH($R^5$)—X—CH($R^5$)— wherein X is N or CH, and each $R^5$, independently, is H, halo, alkyl, or haloalkyl; or A is —P($R^6$)$_2$—, wherein each $R^6$, independently, is alkyl; and
L represents the ligand including the thiol.

20. The method of claim 19, wherein the transition metal complex has the formula:

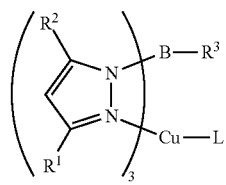

wherein:
each $R^1$, independently, is H, methyl, or trifluoromethyl;
each $R^2$, independently, is H, methyl, trifluoromethyl, or phenyl;
$R^3$ is H or methyl; and
L is the ligand including the thiol.

* * * * *